United States Patent [19]

Tsuruoka et al.

[11] Patent Number: 4,758,557
[45] Date of Patent: Jul. 19, 1988

[54] CEPHALOSPORIN DERIVATIVES AND BACTERICIDES CONTAINING THE SAME

[75] Inventors: Takashi Tsuruoka, Kawasaki; Katsuyoshi Iwamatsu; Kiyoaki Katano, both of Yokohama; Hiroko Ogino, Kawasaki; Ryoichi Okamoto, Chiba; Takashi Yoshida; Masaji Sezaki, both of Tokyo; Fumio Kai, Fujisawa; Shigeharu Inoue; Shinichi Kondo, both of Yokohama, all of Japan

[73] Assignee: Meiji Seika Kaisha, Ltd., Tokyo, Japan

[21] Appl. No.: 872,316

[22] Filed: Jun. 9, 1986

[30] Foreign Application Priority Data

Jun. 26, 1985 [JP] Japan ................ 60-140989
Oct. 26, 1985 [JP] Japan ................ 60-240276

[51] Int. Cl.⁴ ................ C07D 501/36; A61K 31/545
[52] U.S. Cl. ................ 514/206; 540/225; 540/226; 540/227
[58] Field of Search ................ 514/206; 540/227, 226, 540/225

[56] References Cited

U.S. PATENT DOCUMENTS 4,265,892  5/1981  Kocsis et al. ................ 540/227
4,370,327  1/1983  Wetz et al. ................ 540/227
4,393,058  7/1983  Makabe et al. ................ 514/206
4,547,494  10/1985 Oine et al. ................ 514/204

FOREIGN PATENT DOCUMENTS 0139387A  1/1983  Japan.
118792  7/1984  Japan.

OTHER PUBLICATIONS

Ichimoto et al., Agr. Biol. Chem., vol. 31, No. 8, pp. 979–989 (1967).
Heterocyclic Compounds, Pyridine and Derivatives, vol. 14, Parts I thru IV, Published by Interscience Publishers, (1975).
Ochiai et al., Journ. of Antibiotics, pp. 1022–1030, (1980).
Earl et al., Journ. of Org. Chem., 4787–4799 (1984).

Primary Examiner—Nicholas S. Rizzo
Attorney, Agent, or Firm—Frank J. Jordan; C. Bruce Hamburg; Manabu Kanesaka

[57] ABSTRACT

Cephalosporin compounds represented by the following formula (I) and pharmaceutically acceptable salts thereof have a broad bactericidal spectrum against various pathogenic bacteria including Psuedomonas aeruginosa and are useful as bactericidal remedies for pathogenic diseases of human and animals:

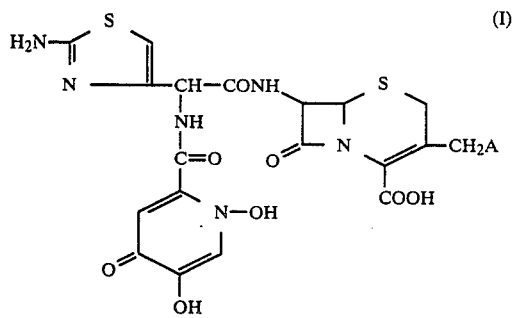

wherein A represents an unsubstituted or substituted pyridylthio group of a formula (I-1);

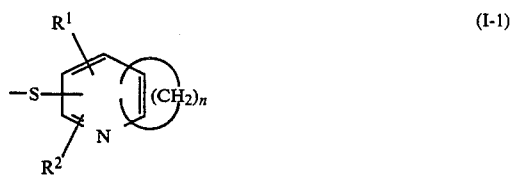

or an unsubstituted or substituted pyridiniumthio group of a formula (I-2):

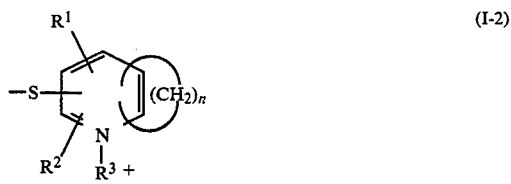

or an unsubstituted or substituted pyridinium group of a formula (I-3);

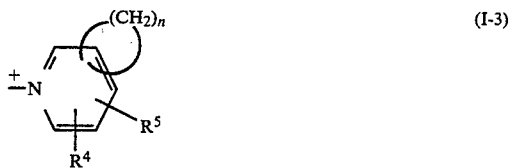

or a 5- or 6-membered heterocyclicthio or bicycloheterocyclicthio group of a formula (I-4):

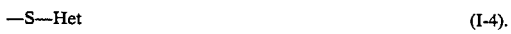

17 Claims, No Drawings

CEPHALOSPORIN DERIVATIVES AND BACTERICIDES CONTAINING THE SAME

FIELD OF THE INVENTION

The present invention relates to new cephalosporin derivatives having a broad bactericidal spectrum against various bacteria including *Pseudomonas aeruginosa*, more precisely, to those having a 2-(2-aminothiazol-4-yl)-2-(1,5-dihydroxy-4-pyridone-2-carboxamido)acetamido group in the 7-position; and the new derivatives have an excellent remedial effect for pathogenic diseases of human and animals and therefore are useful as medicines for human and animals.

BACKGROUND OF THE INVENTION

Cephalosporin antibiotics are widely used for the remedy of diseases caused by pathogenic bacteria, and these are said to be effective for the remedy of diseases caused by such bacteria as tolerant to any other antibiotics such as penicillin-type antibiotics. Regarding the remedial effect of these antibiotics in clinical use, however, the effect can hardly be said sufficient even in the case of so-called cephem-type antibiotics of the third generation which have recently been developed as antibiotics against gram-negative bacteria including opportunistic pathogens.

For instance, cephalosporin derivatives in which the 2-amino group in the 7-aminothiazolylglycyl group is amidated with dihdroxybenzoic acid to form an amido-substituted compound are noted to have a strong bactericidal activity against *Pseudomonas aeruginosa* (refer to Japanese patent application OPI No. 139387/84; the term "OPI" as used herein means an "unexamined published application"), but these are defective as being easily O-methylated and deactivated in a living body.

Japanese patent application OPI No. 118792/84 discloses one example of cephalosporin antibiotics, in which the 2-amino group in the 7-aminothiazolylglycyl group is amidated into 5-hydroxy-4-pyridone-2-carboxamide derivative. However, this essentially discloses carbacephem-type antibiotics, and any concrete examples of 1,5-dihydroxy-4-pyridone-2-carboxamide substituents of the present invention are not described at all in said patent publication.

The synthesis of the 1,5-dihydroxy-4-pyridone-2-carboxylic acid, which is one constitutional element in the 7-positioned substituent of the derivatives of the present invention, is not so easy. This is because N-aminopyridone compounds cannot almost be obtained by the reaction of a kojic acid and a hydrazine (refer to "Agr. Biol. Chem", Vol. 31, pp. 979–989, written by I. Ichimoto, et al. in 1967); and thus, when a pyrone ring is reacted with a hydroxyl-amine, not only the hydroxylamine-substitution on the intended oxygen atom but also the hydroxylamine-substitution on the carbonyl group is generally observed (refer to "Heterocyclic Compounds, Pyridine and its Derivatives", Vol. 14, Part 2, published by Interscience Publishers Ltd.).

Under the circumstances, the present inventors have earnestly studied various relevant techniques and have found that the said compound may be obtained in a relatively high yield by carrying out the reaction in the presence of pyridine or the like compound.

The compounds of the present invention are characterized by the existence of the 1,5-dihydroxy-4-pyridone-2-carboxamido group in the 7-positioned substituent therein; and the present compounds have an unexpectedly intensified and higher bacterial activity against various bacteria, especially against *Pseudomonas aeruginosa*, than the known 5-hydroxy-4-pyridone-2-carboxamido-substituted derivatives, and further, the present compounds have higher solubility in water, which is an important matter for injections. The present invention provides the new cephalosporin derivatives and concretely illustrates hereinafter the preparation and the use of these derivatives.

SUMMARY OF THE INVENTION

The object of the present invention is to provide new cephalosporin antibiotic derivatives and pharmaceutically acceptable salts thereof, which are free from the defects of other conventional cephalosporin antibiotics.

Accordingly, the present invention provides new cephalosporin compounds represented by the following general formula (I) and pharmaceutically acceptable salts thereof as well as bactericides containing the same as an active ingredient:

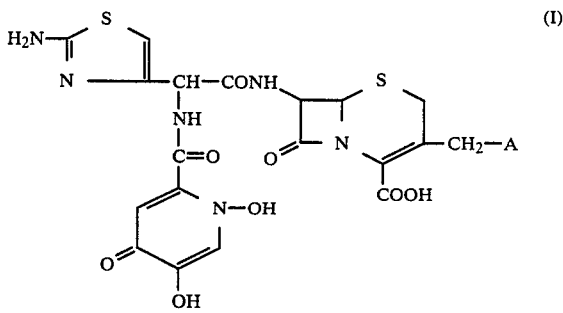

wherein A represents an alkanoyloxy group having 2–5 carbon atoms; a carbamoyloxy group; an azido group; or an unsubstituted or substituted pyridylthio group of a formula (I-1):

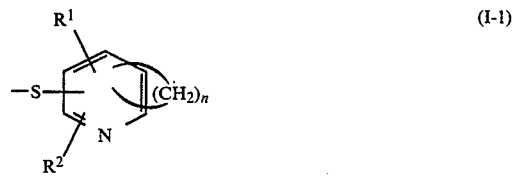

(where n is 0 or an integer of 3–5; $R^1$ and $R^2$ may be the same or different and each represent a hydrogen atom, a halogen atom, a carboxyl group or an optionally halogen-substituted loweralkyl group having 1–5 carbon atoms); or an unsubstituted or substituted pyridiniumthio group of a formula (I-2):

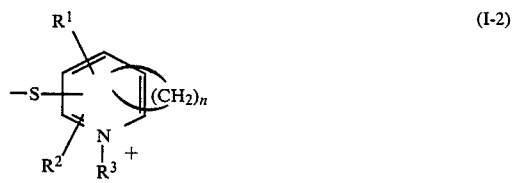

[where n, $R^1$ and $R^2$ have the same meanings as above; $R^3$ represents a linear or branched alkyl group having 1–5 carbon atoms, a halogen-substituted alkyl group, a cyclopropyl group, a cyclopropylmethyl group, an alkenyl group, an oxygen atom or a group of —(CH$_2$-

)$_m$—B; (m is an integer of 0-3; and B represents a hydroxyl group, an alkoxy group, an amino group, an alkyl-substituted amino group, a carboxyl group, a carbamoyl group, a sulfonic acid group, a sulfonic acid amide group, a hydroxamic acid group, a cyano group, a thiol group, an alkylthio group, a methanesulfonylaminocarbonyl group or an acetamidosulfonyl group)]; or an unsubstituted or substituted pyridinium group of a formula (I-3):

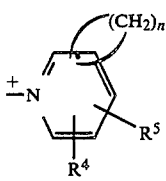

(I-3)

(where n has the same meaning as above; $R^4$ and $R^5$ may be the same or different and each represent a hydrogen atom, a linear or branched alkyl group having 1-5 carbon atoms, a carboxyl group, a carbamoyl group, a sulfonic acid group, a sulfonic acid amide group, a linear or branched alkylthio group having 1-5 carbon atoms, a halogen-substituted alkylthio group, a cycloalkanothio group, a cycloalkanomethylthio group, a carboxyalkylthio group, a carbamoylalkylthio group, an alkoxyalkylthio group or an alkyl-substituted aminoalkylthio group); or a 5- or 6-membered heterocyclicthio or bicycloheterocyclicthio group of a formula (I-4):

 (I-4)

(where Het represents an optionally substituted thiazole, isothiazole, 1,2,3-thiadiazole, 1,3,4-thiadiazole, 1,3,4-triazole, 1,2,3,4-tetrazole, pyrimidine, 1,2,4-triazine, benzothiazole, benzimidazole, benzoxazole, 1,3,4-triazaindolidine or 2,3-dihydro-1H-indolidinium group).

DETAILED DESCRIPTION OF THE PREFERRED EMBODIMENTS

The present invention provides new cephalosporin compounds represented by the following general formula (I) and pharmaceutically acceptable salts thereof as well as bactericides containing the same as an active ingredient.

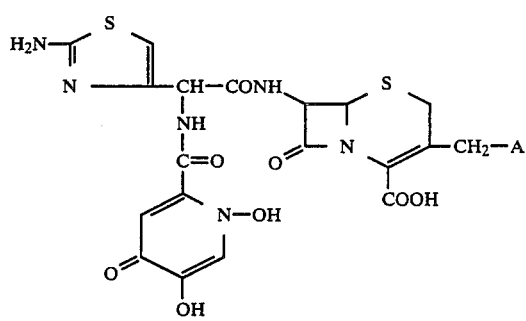

(I)

wherein A represents an alkanoyloxy group having 2-5 carbon atoms; a carbamoyloxy group; an azido group; or an unsubstituted or substituted pyridylthio group of a formula (I-1):

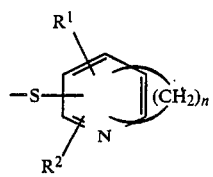

(I-1)

(where n is 0 or an integer of 3-5; $R^1$ and $R^2$ may be the same or different and each represent a hydrogen atom, a halogen atom, a carboxyl group or an optionally halogen-substituted loweralkyl group having 1-5 carbon atoms); or an unsubstituted or substituted pyridiniumthio group of a formula (I-2):

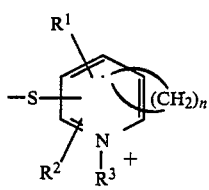

(I-2)

[where n, $R^1$ and $R^2$ have the same meanings as above; $R^3$ represents a linear or branched alkyl group having 1-5 carbon atoms, a halogen-substituted alkyl group, a cyclopropyl group, a cyclopropylmethyl group, an alkenyl group, an oxygen atom or a group of —(CH$_2$)$_m$—B; (m is an integer of 0-3; and B represents a hydroxyl group, an alkoxy group, an amino group, an alkyl-substituted amino group, a carboxyl group, a carbamoyl group, a sulfonic acid group, a sulfonic acid amide group, a hydroxamic acid group, a cyano group, a thiol group, an alkylthio group, a methanesulfonylaminocarbonyl group or an acetamidosulfonyl group)]; or an unsubstituted or substituted pyridinium group of a formula (I-3):

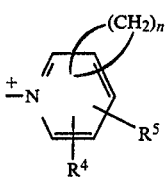

(I-3)

(where n has the same meaning as above; $R^4$ and $R^5$ may be the same or different and each represent a hydrogen atom, a linear or branched alkyl group having 1-5 carbon atoms, a carboxyl group, a carbamoyl group, a sulfonic acid group, a sulfonic acid amide group, a linear or branched alkylthio group having 1-5 carbon atoms, a halogen-substituted alkylthio group, a cycloalkanothio group, a cycloalkanomethylthio group, a carboxyalkylthio group, a carbamoylalkylthio group, an alkoxyalkylthio group or an alkyl-substituted aminoalkylthio group); or a 5- or 6-membered heterocyclicthio or bicycloheterocyclicthio group of a formula (I-4):

 (I-4)

(where Het represents an optionally substituted thiazole, isothiazole, 1,2,3-thiadiazole, 1,3,4-thiadiazole, 1,3,4-triazole, 1,2,3,4-tetrazole, pyrimidine, 1,2,4-triazine, benzothiazole, benzimidazole, benzoxazole, 1,3,4- triazaindolidine or 2,3-dihydro-1-H-indolidinium group).

The α-carbon in the aminothiazolylglycyl substituent in the formula (I) may be in the form of D-isomer or L-isomer, and the present invention includes the both cases of D-isomer and L-isomer as well as DL-isomer.

In addition, the 1,5-dihydroxy-4-pyridone-2-carboxamido part in the 7-positioned substituent of the formula (I) may form the following tautomers, and the present invention includes both the two cases. The nomenclature and the structure of the compounds of the formula (I) are designated herein, based upon the corresponding pyridone-type compounds.

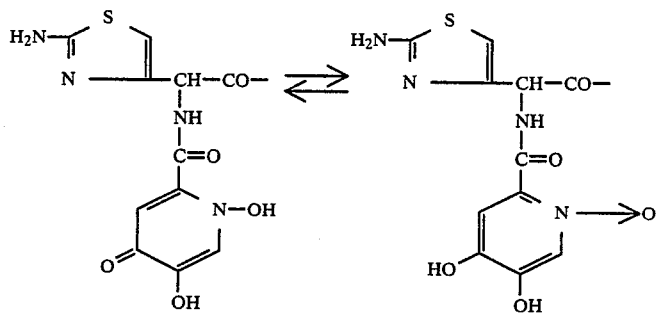

In the present invention, pharmaceutically acceptable salts of the compounds of the above formula (I) include medically acceptable salts, especially conventional non-toxic salts, for example, inorganic salts with an inorganic base such as alkali metal salts (e.g. sodium or potassium salt), alkaline earth metal salts (e.g. calcium or magnesium salt) and ammonium salts, and organic salts with an organic base such as organic amine salts (e.g. triethylamine salt, pyridine salt, ethanolamine salt, triethanolamine salt or dicyclohexylamine salt) and basic amino acid salts (e.g. lysine or arginine salt).

Examples of the 3-positioned substituent of the compounds of the formula (I) of the present invention are given below, which, however, are not whatsoever limitative.

(Pyridin-4-yl)thiomethyl, (pyridin-3-yl)thiomethyl, (pyridin-2-yl)thiomethyl, (3-methoxypyridin-4-yl)thiomethyl, (2,3-dimethylpyridin-4-yl)thiomethyl, (2-carboxypyridin-4-yl)thiomethyl, (2-carbamoylpyridin-4-yl)thiomethyl, (2,3-cyclopentenopyridin-4-yl)thiomethyl, (pyridin-N-oxide-4-yl)thiomethyl, (2,3-cyclopentenopyridin-N-oxide-4-yl)thiomethyl, (5,6-cyclopentenopyridin-2-yl)thiomethyl, (2,3-cyclohexenopyridin-4-yl)thiomethyl, (5,6-cyclohexenopyridin-2-yl)thiomethyl, (1-methylpyridinium-4-yl)thiomethyl, (1-methylpyridinium-3-yl)thiomethyl, (1-methylpyridinium-2-yl)thiomethyl, (1-ethylpyridinium-4-yl)thiomethyl, (1-allylpyridinium-4-yl)thiomethyl, [1-(2,2,2-trifluoroethyl)pyridinium-4-yl]thiomethyl, (1-carboxymethylpyridinium-4-yl)thiomethyl, (1-carbamoylmethylpyridinium-4-yl)thiomethyl, (1-hydroxyethylpyridinium-4-yl)thiomethyl, (1-dimethylaminoethylpyridinium-4-yl)thiomethyl, (1-cyclopropylpyridinium-4-yl)thiomethyl, (1-cyclopropylmethylpyridnium-4-yl)thiomethyl, (1-methylthiomethylpyridinium-4-yl)thiomethyl, (1-cyanomethylpyridinium-4-yl)thiomethyl, [1-(2-fluoroethyl)pyridinium-4yl]thiomethyl, (1-hydroxyaminocarbonylmethylpyridinium-4-yl)thiomethyl, [1-(2-sulfoethyl)pyridinium-4-yl]thiomethyl, (1-sulfomethylpyridinium-4-yl)thiomethyl, [1-(2-sulfamoylethyl)pyridinium-4-yl]thiomethyl, (1-sulfamoylmethylpyridinium-4-yl)thiomethyl, (1-N,N-dimethylsulfamoylmethylpyridinium-4-yl)thiomethyl. [2-methyl-1-(2-hydroxyethyl)pyridinium-4-yl]thiomethyl, (2,6-dimethyl-1-carboxymethylpyridinium-4-yl)thiomethyl, (3,5-dimethyl-1-carboxymethylpyridinium-4-yl)thiomethyl, (2-carboxy-1-methylpyridinium-4-yl)thiomethyl, (2,3-dihydro-1H-indolidinium-5-yl)thiomethyl, (1-ethylpyridinium-3-yl)thiomethyl, (1-cyclopropylpyridinium-3-yl)thiomethyl, [1-(2-hydroxyethyl)pyridinium-3-yl]thiomethyl, (1-carboxymethylpyridinium-3-yl)thiomethyl, (1-carbamoylmethylpyridinium-3-yl)thiomethyl, [1-(2-fluoroethyl)pyridinium-3-yl]thiomethyl, [1-(2,2,2-trifluoroethyl)pyridinium-3-yl]thiomethyl, (1-sulfomethylpyridinium-3-yl)thiomethyl, (1-sulfamoylmethylpyridinium-3-yl)thiomethyl, [1-(2-sulfoethyl)pyridinium-3-yl]thiomethyl, (1-cyclopropylpyridinium-2-yl)thiomethyl, [1-(2-hydroxyethyl)pyridinium-2-yl]thiomethyl, (1-carboxymethylpyridinium-2-yl)thiomethyl, (1-carbamoylmethylpyridinium-2-yl)thiomethyl, (1-sulfomethylpyridinium-2-yl)thiomethyl, (2,3-cyclopenteno-1-methylpyridinium-4-yl)thiomethyl, (2,3-cyclopenteno-1-ethylpyridinium-4-yl)thiomethyl, (2,3-cyclopenteno-1-allylpyridinium-4-yl)thiomethyl, [2,3-cyclopenteno-1-(2,2,2-trifluoroethyl)pyridinium-4-yl]thiomethyl, (2,3-cyclopenteno-1-carboxymethylpyridinium-4-yl)thiomethyl, (2,3-cyclopenteno-1-carbamoylmethylpyridinium-4-yl)thiomethyl, [2,3-cyclopenteno-1-(2-hydroxyethyl)pyridinium-4-yl)thiomethyl, (2,3-cyclopenteno-1-dimethylaminoethylpyridinium-4-yl)thiomethyl, (2,3-cyclopenteno-1-cyclopropylpyridinium-4-yl)thiomethyl, (2,3-cyclopenteno-1-cyclopropylmethylpyridinium-4-yl)thiomethyl, (2,3-cyclopenteno-1-cyanomethylpyridinium-4-yl)thiomethyl, (5,6-cyclopenteno-1-methylpyridinium-2-yl)thiomethyl, (5,6-cyclopenteno-1-carboxyethylpyridinium-2-yl)thiomethyl, [5,6-cyclopenteno-1-(2-hydroxyethyl)pyridinium-2-yl]thiomethyl, (2,3-cyclohexeno-1-methylpyridinium-4-yl)thiomethyl, (2,3-cyclohexeno-1-carboxyethylpyridinium-4-yl)thiomethyl, (2,3-cyclohexeno-1-carbamoylmethylpyridinium-4-yl)thiomethyl, [2,3-cyclohexeno-1-(2-hydroxyethyl)pyridinium-4-yl]thiomethyl, [2,3-cyclohexeno-1-(dimethylaminoethyl)pyridinium-4-yl]thiomethyl, pyridiniummethyl, 4-methylpyridiniummethyl, 2,3-dimethylpyridiniummethyl, 2,3-cyclopentenopyridiniummethyl, 2,3-cyclohexenopyridiniummethyl, 4-carbamoylpyridiniummethyl, 3-carbamoylpyridiniummethyl, 4-methylthiopyridiniummethyl, 3-methylthiopyridiniummethyl, 2-methylthiopyridiniummethyl, 4-ethylthiopyridiniummethyl, 4-allylthiopyridiniummethyl, 4-cyclopropylmethylthiopyridiniummethyl, 3-cyclopropylmethylthiopyridiniummethyl, 4-cyclopropylthiopyridiniummethyl, 4-cyclopentylthiopyridiniummethyl, 4-(2,2,2-trifluoroethyl)thiopyridiniummethyl, 4-(2-hydroxyethyl)thiopyridiniummethyl, 3-(2-hydroxyethyl)thiopyridiummethyl, 4-(2-fluoroethyl)thiopyridiniummethyl, 4-carboxyethylthiopyridiniummethyl, 4-carbamoylethylthiopyridiniummethyl, 4-(N,N-dimethylaminoethyl)thiopyridiniummethyl, 2,3-cyclopenteno-4-methylthiopyridiniummethyl, 2,3-cyclopenteno-4-ethylthiopyridiniummethyl, 2,3-cyclopenteno-4-allylthiopyridiniummethyl, 2,3-cyclopenteno-4-cyclopropylmethylthiopyridiniummethyl, 2,3-cyclopenteno-2-cyclopropylthiopyridiniummethyl, 2,3-cyclopenteno-4-pentylthiopyridiniummethyl, 2,3-cyclopenteno-4-(2,2,2-trifluoroethyl)thiopyridiniummethyl, 2,3-cyclopenteno-4-(2-hydroxyethyl)thiopyridiniummethyl, 2,3-cyclopenteno-4-(2-fluoroethyl)thiopyridiniummethyl, 2,3-cyclopenteno-4-carboxymethylthiopyridiniummethyl, 2,3-cyclopenteno-4-carbamoylmethylthiopyridiniummethyl, 2,3-cyclopenteno-4-(N,N-dimethylaminoethyl)thiopyridiniummethyl, 2,3-cyclohexeno-4-methylthiopyridiniummethyl, 2,3-cyclohexeno-4-cyclopropylmethylthiopyridiniummethyl, 2,3-cyclohexeno-4-(2,2,2-trifluoroethyl)thiopyridiniummethyl, (1H-tetrazol-5-yl)thiomethyl, (1-methyl-1H-tetrazol-5-yl)thiomethyl, (1-amino-1H-tetrazol-5-yl)thiomethyl, [1-(2-dimethylaminoethyl)-1H-tetrazol-5-yl]thiomethyl, [1-(2-hydroxyethyl)-1H-tetrazol-5-yl]thiomethyl, [1-(2-carboxyethyl)-1H-tetrazol-5-yl]thiomethyl, (1-carboxymethyl-1H-tetrazol-5-yl)thiomethyl, (1-carbamoylmethyl-1H-tetrazol-5-yl)thiomethyl, (1-sulfomethyl-1H-tetrazol-5-yl)thiomethyl, [1-(2-sulfoethyl)-1H-tetrazol-5-yl]thiomethyl, (1-sulfamoyl-methyl-1H-tetrazol-5-yl)thiomethyl, (1,3,4-thiadiazol-5-yl)thiomethyl, (2-methyl-1,3,4-thiadiazol-5-yl)thiomethyl, (2-trifluoromethyl-1,3,4-thiadiazol-5-yl)thiomethyl, (2-carboxy-1,3,4-thiadiazol-5-yl)thiomethyl, (2-carboxymethyl-1,3,4-thiadiazol-5-yl)thiomethyl, (2-methylamino-1,3,4-thiadiazol-5-yl)thiomethyl, (2-amino-1,3,4-thiadiazol-5-yl)thiomethyl, (2-mercapto-1,3,4-thiadiazol-5-yl)thiomethyl, (2-carbamoylmethyl-1,3,4-thiadiazol-5-yl)thiomethyl, (1,2,3-thiadiazol-5-yl)thiomethyl, (1,2,4-thiadiazol-5-yl)thiomethyl, (3-methyl-1,2,4-thiadiazol-5-yl)thiomethyl, (3-phenyl-1,2,4-thiadiazol-5-yl)thiomethyl, (thiazol-2-yl)thiomethyl, (4-methylthiazol-2-yl)thiomethyl, (4-phenylthiazol-2-yl)thiomethyl, (4-trifluoromethylthiazol-2-yl)thiomethyl, (4-carboxymethylthiazol-2-yl)thiomethyl, (5-methylthiazol-2-yl)thiomethyl, (5-phenylthiazol-2-yl)thiomethyl, (4-carboxy-3-hydroxy-isothiazol-5-yl)thiomethyl, (4-cyano-3-hydroxylsothiazol-5-yl)thiomethyl, (1,3,4-oxadiazol-5-yl)thiomethyl, (2-methyl-1,3,4-oxadiazol-5-yl)thiomethyl, (2-phenyl-1,3,4-oxadiazol-5-yl)thiomethyl, (2-carboxymethyl-1,3,4-oxadiazol-5-yl)thiomethyl, (1,2,4-oxadiazol-5-yl)thiomethyl, (3-methyl-1,2,4-oxadiazol-5-yl)thiomethyl, (3-phenyl-1,3,4-oxadiazol-5-yl)thiomethyl, (pyrazol-5-yl)thiomethyl, (1-methylimidazol-2-yl)thiomethyl, (1H-1,2,3-triazol-5-yl)thiomethyl, (1-methyl-1H-1,2,3-triazol-5-yl)thiomethyl, (1H-1,2,4-triazol-5-yl)thiomethyl, (1-methyl-1H-1,2,4-triazol-5-yl)thiomethyl, (4-methyl-3-trifluoromethyl-4H-1,2,4-triazol-5-yl)thiomethyl, (1H-1,3,4-triazol-5-yl)thiomethyl, (1-methyl-1H-1,3,4-triazol-5-yl)thiomethyl, (1-carboxymethyl-1H-1,3,4-triazol-5-yl)thiomethyl, (1-carbamoylmethyl-1H-1,3,4-triazol-5-yl)thiomethyl, (2-methyl-1H-1,3,4-triazol-5-yl)thiomethyl, (2-carboxymethyl-1H-1,3,4-triazol-5-yl)thiomethyl, (2-phenyl-1H-1,3,4-triazol-5-yl)thiomethyl, (2,5-dihydro-2-methyl-5-oxo-6-hydroxy-1,2,4-triazin-3-yl)thiomethyl, (4,5-dihydro-4-methyl-5-oxo-6-hydroxy-1,2,4-triazin-3-yl)thiomethyl, (pyridazin-3-yl)thiomethyl, (2-oxypyridazin-3-yl)thiomethyl, (pyrimidin-2-yl)thiomethyl, (benzothiazol-2-yl)thiomethyl, (benzimidazol-2-yl)thiomethyl, (benzoxazol-2-yl)thiomethyl, (3H-4-quinazolinon-2-yl)thiomethyl, (5-methyl-s-triazolo[1,5-a]pyrimi-din-7-yl)thiomethyl.

The synthesis of the above-mentioned 3-substituents may be carried out in accordance with a known method, as described in "Heterocyclic Compounds, Pyridine and its Derivatives", Vol. 14, Parts I through IV (published by Interscience Publishers Ltd.). In particular, the synthesis of cyclo-ring-containing compounds such as cycloalkanothiopyridones and substituted alkylthiocycloalkanopyridines was carried out in the present invention, in accordance with the method as described in the applicant's own Japanese Patent Application Nos. 33747/84, 138206/84 and 254518/84.

For the synthesis of the 1,5-dihydroxy-4-pyridone-2-carboxylic acid, which is a constitutional element of the 7-substituent in the compounds of the formula (I), or protected compounds thereof; (a) a protected 5-hydroxy-4-pyrone-2-carboxylic acid is reacted with a hydroxylamino acid salt in the presence of pyridine or the like compound, as follows:

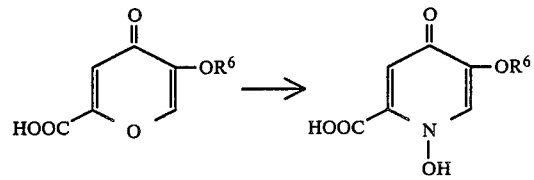

In these formulae, $R^6$ represents a removable protective group such as benzyl, p-nitrobenzyl, o-nitrobenzyl, p-methoxybenzyl or phenacyl group.

Alternatively, (b) a halogen-substituted derivative of 5-hydroxy-4-pyridone-2-carboxylic acid is oxidized with hydrogen peroxide or the like to obtain the corresponding N-oxide, which is thereafter hydrolyzed, as follows:

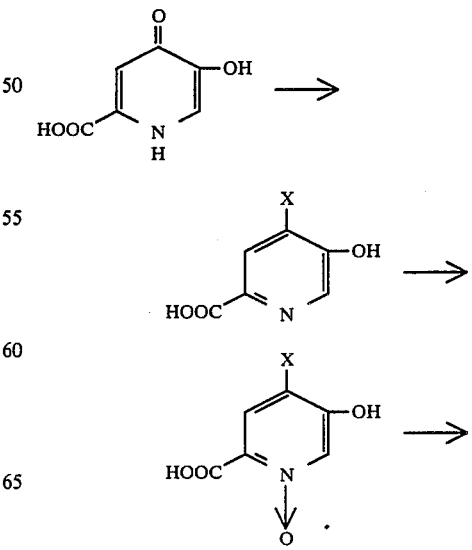

-continued

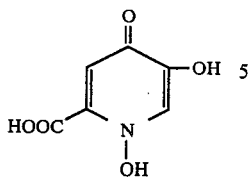

(wherein X represents a halogen atom).

The cephalosporin compound of the general formula (I) of the present invention may be prepared, according to the following method of (A), (B) or (C):

(A) A compound of a general formula (II) or a salt or silylated compound thereof:

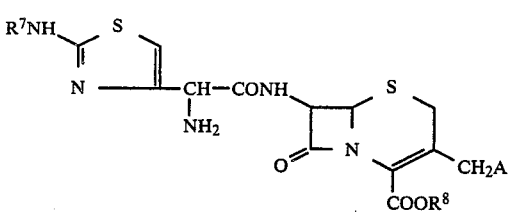

(where $R^7$ represents a hydrogen atom or an amino-protective group; $R^8$ represents a hydrogen atom or a carboxylprotective group; and A has the same meaning as above) is reacted with a compound of a general formula (III) or a carboxyl-reactive derivative thereof:

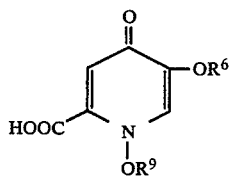

(where $R^6$ and $R^9$ may be the same or different and each represents a hydrogen atom or a removable protective group such as benzyl, p-nitrobenzyl, o-nitrobenzyl, p-methoxybenzyl, methoxyethyoxymethyl or phenacyl), and then, if necessary, the protective group(s) is(are) removed, to obtain the compounds of the formula (I).

(B) A compound of a general formula (IV):

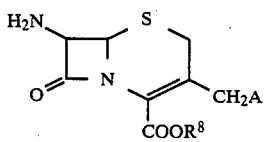

(where $R^8$ and A have the same meanings as above) is reacted with a compound of a general formula (V) or a carboxylreactive derivative thereof:

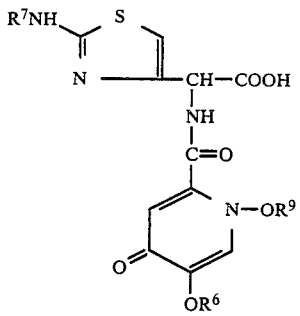

(where $R^6$, $R^7$ and $R^9$ have the same meanings as above), and then, if necessary, the protective group(s) is(are) removed, to obtain the compounds of the formula (I).

(C) A compound of a general formula (VI):

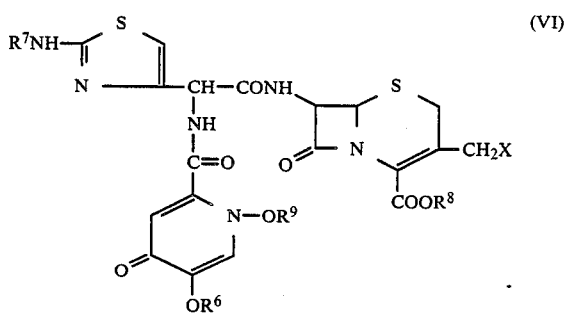

(where $R^6$, $R^7$, $R^8$ and $R^9$ have the same meanings as above; and X represents an acetoxy group or a halogen atom) is reacted with a compound selected from formulas (VII) through (X):

a general formula

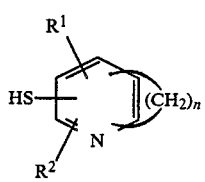

a general formula

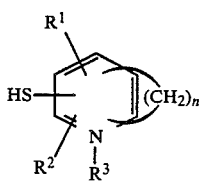

a general formula

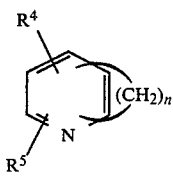

a general formula $$-S-Het \quad (X)$$

(where n, $R^1$, $R^2$, $R^3$, $R^4$, $R^5$ and Het have the same meanings as above), and then, if necessary, the protective group(s) is(are) removed to obtain the compounds of the formula (I).

Regarding the amino-protective group and the carboxylprotective group in the above formulae, any conventional groups which are generally used in the field of synthesis of β-lactams and peptides for this purpose of protection of amino or carboxyl group may appropriately be adapted to the present processes (A) through (C).

Examples of amino-protective groups include phthaloyl, formyl, monochloroacetyl, dichloroacetyl, trichloroacetyl, methoxycarbonyl, ethoxycarbonyl, t-butoxycarbonyl, trichloroethoxycarbonyl, benzyloxycarbonyl, p-nitrobenzyloxycarbonyl, diphenylmethyloxycarbonyl, methoxymethyloxycarobnyl, trityl and trimethylsilyl groups; and examples of carboxylprotective groups are t-butyl, t-amyl, benzyl, p-nitrobenzyl, p-methoxybenzyl, benzhydryl, phenyl, p-nitrophenyl, methoxymethyl, ethoxymethyl, benzyloxymethyl, acetoxymethyl, methylthiomethyl, trityl, trichloroethyl, trimethylsilyl, dimethylsilyl and dimethylaminoethyl groups.

In the methods (A) and (B), the basic reaction is a condensation reaction by acylation, and general means for the acylation of penicillins and cephalosporins are adapted thereto.

Reactive derivatives which may be used in these methods include, for example, acid halides, acid anhydrides, active amides and active esters. Preferred examples thereof are acid chlorides; acid bromides; mixed acid anhydrides with acetic acid, pivalic acid, isovaleric acid or trichloroacetic acid; active amides with pyrazole, imidazole, dimethylpyraozle or benzotriazole; active esters with p-nitrophenyl ester, 2,4-dinitrophenyl ester, trichlorophenyl ester, 1-hydroxy-1H-2-pyridone, N-hydroxysuccinimide or N-hydroxyphthalimide.

In these methods, if the compound of formula (III) or (V) is used in the form of a free acid, the reaction is peferably carried out in the presence of a condensing agent; and examples of usable condensing agents are carbodiimide compounds such as N,N-dicyclohexylcarbodiimide, N-cyclohexyl-N'-morpholinoethylcarbodiimide, N-cyclohexyl-N'-(4-diethylaminocyclohexyl)carbodiimide, and reagents obtained by the reaction of an amide compound (such as N-methylformamide or N,N-dimethylformamide) and a halide (such as thionyl chloride, phosphorus oxychloride or phosgene), the reagents being known as so-called Vilsmeier reagents.

Among the reactive derivatives to be used in the present reaction, acid halides and acid anhydrides indispensably require an acid-binding agent, when reacted; and examples of the acid-binding agents usable in the present reaction with the acid halide or acid anhydride are organic bases such as triethylamine, trimethylamine, ethyldiisopropylamine, N,N-dimethylaniline, N-methylmorpholine and pyridine; alkali metal or alkaline earth metal compounds such as sodium, ptoassium or calcium hydroxide, carbonate or bicarbonate; and oxiranes such as ethyleneoxide and propyleneoxide.

The present reaction is generally carried out in a solvent which does not have any inconvenient influence on the reaction; and examples of usable solvents are water, acetone, acetonitrile, dioxane, textrahydrofuran, methylene chloride, chloroform, dichloroethane, N,N-dimethylformamide or a mixture thereof.

The reaction temperature is not specifically limitative and is generally −30° C. to 40° C.; and the reaction period up to the completion of the reaction is 30 minutes to 10 hours.

In case the acylated products thus obtained have any protective group(s), removal of the protective group(s) is required. For the removal of the protective group, various methods may selectively be carried out in accordance with the kind of the protective group to be removed, including, for example, a method with an acid, a method with a base or a method with a hydrazine. Conventional means which are generally utilized in the field of synthesis of β-lactams and peptides may selectively be adapted to the present removal reaction.

The compounds of the general formula (II), which are an intermediate in the method (A), may be synthesized, according to the method as described in "J. Antibiotics 35, 1022 (1980)".

In the method (C), the reaction of the compound of the formula (VI) with the compound of the formula (VII), (VIII) or (IX) may be carried out in accordance with a conventional process which is generally carried out in the chemical field of cephalosporin compounds. More precisely, in case X in the formula (VI) is an acetoxy group, the reaction is preferably carried out, in general, in a polar solvent such as water, phosphate buffer, acetone, acetonitrile, N,N-dimethylformamide, N,N-dimethylacetamide, tetrahydrofuran, dimethylsulfoxide, dioxane, methanol or ethanol or in a mixture of the solvent and water. The reaction is preferably carried out nearly under neutral condition or so; and the reaction temperature is, though not specifically limitative, preferably from room temperature to about 70° C. or so.

The time required for the completion of the present invention varies, depending upon the reaction condition, and is in general 1–10 hours. The present reaction may be accelerated, when carried out in the presence of an alkali metal halide such as sodium iodide or potassium iodide.

In case the compounds of the present invention are to be obtained from the compound of the formula (VI) where X is a halogen, the halogen may be chlorine, bromine or iodine.

The reaction is generally carried out in a solvent such as acetone, dioxane, tetrahydrofuran, ethyl acetate, acetonitrile, N,N-dimethylformamide or N,N-dimethylacetamide, and preferably under water-free condition. The reaction temperature is, in general, preferably 0°–50° C., and the reaction finishes in 1–5 hours.

The compound of the formula (I) thus obtained as above may be isolated from the reaction mixture in a conventional manner.

For instance, the isolation of the compound of the formula (I) may be carried out by appropriate combination of purification, sedimentation and crystallization with an adsorptive resin such as Amberlite XAD-2 (by Rohm and Haas Co.) or Diaion HP-20 (by Mitsubishi Chemical Industries, Ltd.)

The bactericides containing the compound of the formula (I) or a salt thereof as a main component may be utilized in the form of various preparations, for example, injections such as those for venoclysis or intramuscular application, peroral medicines such as capsules, tablets or granules, or per-rectal medicines, oily and fatty suppositories, water-soluble suppositories or the like various shaped medicines. These preparations may be manufactured in a conventional manner, using The acute toxicity of the compound of the formula (I) was measured by using mouse and the $LD_{50}$ value was more than 1 g/kg.

TABLE 1

| | MIC in agar plate culture-dilution assay (Y/ml) | | | | | |
|---|---|---|---|---|---|---|
| Test organisms | Compound of Example 4 | Compound of Example 5 | Compound of Example 6 | Compound of Example 8 | Compound of Example 14 | Compound of Example 15 |
| Staphylococcus aureus 209P JC-1 | 3.13 | 1.56 | 1.56 | 1.56 | 1.56 | 1.56 |
| Staphylococcus aureus Smith (1) | 3.13 | 3.13 | 3.13 | 1.56 | 1.56 | 3.13 |
| Bacillus subtilis ATCC 6633 | 12.5 | 3.13 | 3.13 | 3.13 | 6.25 | 3.13 |
| Escherichia coli NIHJ JC-2 | 0.10 | 0.05 | 0.05 | 0.05 | 0.05 | 0.10 |
| Klebsiella pneumoniae GN-69 | 0.10 | 0.05 | 0.10 | 0.05 | <0.025 | 0.05 |
| Proteus vulgaris GN-76 | 0.39 | 0.39 | 0.20 | 0.20 | 0.10 | 0.10 |
| Proteus rettgeri GN-624 | 0.20 | 0.10 | 0.20 | 0.10 | 0.10 | 0.20 |
| Citrobacter freundii GN-346 | 6.25 | 0.78 | 1.56 | 0.78 | 0.10 | 0.20 |
| Enterobacter cloacae GN-7471 | 3.13 | 1.56 | 1.56 | 1.56 | 0.78 | 0.78 |
| Serratia marcescens No. 1 | 0.20 | 0.20 | 0.20 | 0.20 | 0.10 | 0.39 |
| Pseudomonas aeruginosa M-0148 | 0.39 | 0.78 | 0.78 | 1.56 | 0.20 | 0.20 |
| Pseudomonas aeruginosa E-2 | 0.10 | 0.05 | 0.05 | 0.10 | <0.025 | <0.025 |
| Pseudomonas aeruginosa IAM-1007 | 0.20 | 0.10 | 0.10 | 0.20 | <0.025 | 0.20 |
| Pseudomonas maltophilia M-0627 | — | — | — | — | 6.25 | 0.78 |

| Test organisms | Compound of Example 16 | Compound of Example 17 | Compound of Example 22 | Compound of Example 25 | Compound of Example 26 | A | B |
|---|---|---|---|---|---|---|---|
| Staphylococcus aureus 209P JC-1 | 3.13 | 3.13 | 3.13 | 3.13 | 3.13 | 0.78 | 3.13 |
| Staphylococcus aureus Smith (1) | 3.13 | 3.13 | 3.13 | 6.25 | 3.13 | 0.78 | 3.13 |
| Bacillus subtilis ATCC 6633 | 6.25 | 3.13 | 3.13 | 3.13 | 3.13 | 1.56 | 6.25 |
| Escherichia coli NIHJ JC-2 | 0.10 | <0.025 | 0.05 | 0.05 | 0.10 | 0.10 | 0.20 |
| Klebsiella pneumoniae GN-69 | 0.20 | 0.10 | 0.05 | 0.05 | 0.05 | 0.20 | 0.10 |
| Proteus vulgaris GN-76 | 0.39 | 0.20 | 0.10 | 0.10 | 0.20 | 0.78 | 0.05 |
| Proteus rettgeri GN-624 | 1.56 | 0.10 | 0.20 | 3.13 | 3.13 | 1.56 | 0.39 |
| Citrobacter freundii GN-346 | 0.78 | 0.78 | 0.39 | 0.78 | 0.39 | 0.39 | 0.78 |
| Enterobacter cloacae GN-7471 | 1.56 | 0.78 | 0.78 | 6.25 | 1.56 | 3.13 | 3.13 |
| Serratia marcescens No. 1 | 0.39 | 0.20 | 0.20 | 0.20 | 0.78 | 0.20 | <0.025 |
| Pseudomonas aeruginosa M-0148 | 3.13 | 1.56 | 0.39 | 0.20 | 0.20 | 50 | 3.13 |
| Pseudomonas aeruginosa E-2 | 0.10 | 0.10 | 0.10 | 0.05 | 0.05 | 0.20 | 1.56 |
| Pseudomonas aeruginosa IAM-1007 | <0.025 | 0.05 | 0.39 | 0.10 | 0.20 | 6.25 | 1.56 |
| Pseudomonas maltophilia M-0627 | 6.25 | 6.25 | 1.56 | 1.56 | 3.13 | 50 | 50 |

A; (6R,7R)7-[(RS)—2-(2-aminothiazol-4-yl)-2-(5-hydroxy-4-pyridone-2-carboxamido)acetamido]-3-(1-metylpyridinium-4-thiomethyl-ceph-3-em-4-carboxylate
B; ceftazidime conventional vehicle, extender, binder, moistener, disintegrator, surfactant, lubricant, dispersing agent, buffer, preservative, solubilization-assistant, antiseptic, flavour, pain-removing agent, etc. Concrete examples for the manufacture of the present bactericidal preparations are given hereinafter in detail.

The dose of the preparation is properly determined case by case, under the consideration of the condition, age and sex of patients; and in general, the proper dose is 250-3000 mg/day/adult, and this is administered to the patient as divided into 1-4 times a day.

The compounds of the formula (I) and salts thereof of the present invention are new, and have high and broad antibacterial activity capable of inhibiting the growth of pathogenic microorganisms of a broad range including gram-positive and gram-negative bacteria. In order to show the usability of the compounds of the formula (I), the antibacterial activity of some typical compounds of the formula (I) was actually measured, and the results are given in the following Table-1.

The cephalosporin derivatives of the present invention, having the 7-positioned 2-(2-aminothiazol-4-yl)-2-(1,5-dihydroxy-4-pyridone-2-carboxamino)acetamido substituent, show a broad antibacterial activity because of the synergestic effect of the 7-positioned substituent and the 3-positioned substituent; and in particular, these are especially highly active against Pseudomonas aeruginosa, and have high water-solubility which is an imporant element for injections.

The present invention will be explained in greater detail by reference to the following examples, which, however, are not intended to be interpreted as limiting the scope of the present invention. It is a matter of course that various changes and modifications can be made in the present invention without departing from the spirit and scope thereof.

In the Examples and Referential Examples, NMR data were based upon 100 MHz- or 400 MHz-NMR, and unless otherwise specifically indicated, $\delta$-value in a deuterium oxide was an index as based upon the $\delta$-value (=4.82) of the peak of water and $\delta$-value in the other deuterated solvent was one as based upon the standard of TMS.

REFERENTIAL EXAMPLE 1

1,5-Dihydroxy-4-pyridone-2-carboxylic acid (a) 3.45 g of sodium was added to 200 ml of anhydrous methanol, to prepare a sodium methoxide solution. At room temperature, 21.3 g of kojic acid was added thereto and then 19 ml of benzyl chloride was added dropwise thereto, and thereafter the whole was heated under reflux and reacted for 4 hours.

After the reaction, the reaction solution was concentrated, 200 ml of water was added to the remaining residue and the precipitated crystal was taken out by filtration and washed with water and ether and then dried to obtain 29 g of 5-benzyloxy-2-hydroxymethyl-4-pyrone.

16 g of the product was dissolved in 600 ml of methanol, and 100 g of active manganese dioxide was added thereto and reacted for 1 hour while heated under reflux. After the reaction, the insoluble part was filtrated out, and the remaining filtrate solution was concentrated under reduced pressure to about 200 ml. To this were added 200 ml of water, 69 ml of 1N-NaOH and 15.9 g of silver oxide, and reacted for 30 minutes at room temperature. After the reaction, the insoluble part was filtrated out, and the remaining filtrate was concentrated under reduced pressure to remove methanol therefrom and then washed with dichloromethane, and 77.5 ml of 1N-HCl was added thereto to form a precipitate, which was taken out by filtration, washed with water and dried, to obtain 13 g of 5-benzyloxy-4-pyrone-2-carboxylic acid.

NMR (DMSO-$d_6$) δ: 4.99(2H, s), 7.41(5H, m), 6.92(1H, s), 8.35(1H, s).

(b) 4.92 g of 5-benzyloxy-4-pyrone-2-carboxylic acid was dissolved in 70 ml of pyridine, and 7 g of hydroxylamine hydrochloride was added thereto and reacted for 2 hours at 80° C. After the reaction, the reaction solution was concentrated under reduced pressure, 250 ml of water was added to the remaining residue, and the resulting solution was regulated to have a pH value of 1.5–2.0 with 6N-HCl while cooled with ice, and then this was stirred for 30 minutes at the same temperature. The precipitate formed was taken out by filtration, washed with water and dried to obtain 2.5 g of 5-benzyloxy-1-hydroxy-4-pyridone-2-carboxylic acid. NMR (DMSO-$d_6$) δ: 5.26(2H, s), 7.35–7.55(5H, m), 7.57(1H, s), 8.55(1H, s).

(c) 2 g of 5-benzyloxy-1-hydroxy-4-pyridone-2-carboxylic acid was suspended in 100 ml of 50%-methanol/water, 1.53 ml of 1N-NaOH was added thereto and dissolved, and 500 mg of 5%-palladium/carbon was added thereto and subjected to catalytic hydrogenation in a hydrogen-gas stream atmosphere at room temperature. After the reaction, 5%-palladium/carbon was filtrated out, and the remaining residue was washed with 50%-methanol/water and concentrated under reduced pressure to remove methanol therefrom, and 8 ml of 1N-HCl was added thereto. The precipitate formed was taken out by filtration, washed with water and dried to obtain 1.2 g of the above entitled compound.

NMR (DMSO-$d_6$) δ 7.55(1H, s), 8.05(1H, s).

REFERENTIAL EXAMPLE 2

5-p-Methoxybenzyloxy-1-hydroxy-4-pyridone-2-carboxylic acid (a) 34.5 q of 5-benzyloxy-4-pyrone-2-carboxylic acid was suspended in 500 ml of concentrated hydrochloric acid and 250 ml of water and reacted for 1 hour at 80° C. The reaction solution was cooled with ice, and the formed crystal was taken out by filtration, washed with water and then dried, to obtain 16.6 g of 5-hydroxy-4-pyrone-2-carboxylic acid.

NMR (DMSO-dl) δ 6.96(1H, s), 8.17(1H, s).

(b) 39.3 g of 5-hydroxy-4-pyrone-2-carboxylic acid was dissolved in 700 ml of DMF, and 62.5 g of potassium-t-butoxide was added thereto, while cooled with ice. After 30 minutes, 75 ml of p-methoxybenzyl chloride was added to the mixture and stirred for 30 minutes at room temperature and then reacted for 24 hours at 60° C.

After the reaction, the reaction solution was added to 2.5 lit. of dichloromethane, washed with water (800 ml×3), dried with magnesium sulfate and then concentrated under reduced pressure to a little amount. Afterwards, 350 ml of ether was added to the resulting residue and the crystal as precipitated was taken out by filtration, washed with ether and dried to obtain 75 g of p-methoxybenzyl 5-p-methoxybenzyloxy-4-pyrone-2-carboxylate.

NMR(CDCl$_3$) δ: 3.80(3H, S), 3.82(3H, S), 5.02(2H, S) 5.29(2H, s), 6.88(2H, d), 6.92(2H, d), 7.17(1H, s), 7.30(2H, d), 7.34(2H, d), 7.60(1H, s).

(c) 70 g of the product as above obtained was dissolved in 1.87 lit. of tetrahydrofuran, and 476 ml of water and 264 ml of 1N-NaOH were added thereto and reacted for 30 minutes at room temperature. Tetrahydrofuran was removed off from the reaction mixture under reduced pressure, and then 600 ml of water was added to the remaining residue and washed with dichloromethane. Next, 265 ml of 1N-HCl was added thereto, while cooled with ice, and the precipitate as formed was taken out by filtration, washed with water and dried to obtain 34.9 g of 5-p-methoxybenzyloxy-4-pyrone-2-carboxylic acid.

NMR(DMSO-$d_6$) δ: 3.77(3H, s), 4.90(2H, s), 6.92(1H, s), 6.96(2H, d), 7.37(2H, d), 8.34(1H, s).

(d) 33.2 g of 5-methoxybenzyloxy-4-pyrone-2-carboxylic acid was dissolved in 500 ml of pyridine, and 41.7 g of hydroxylamine hydrochloride was added thereto and reacted for 1 hour at 80° C. The reaction solution was concentrated under reduced pressure to a little amount, and 800 ml of water was added to the remaining residue, and the pH value thereof was adjusted to 2 with 6N-HCl, while cooled with ice. The precipitate as formed was taken out by filtration, washed with water and dried to obtain 17.25 g of the above-entitled product.

NMR(DMSO-$d_6$) δ: 3.80(3H, s), 5.22(2H, s), 7.00(2H, d), 7.43(2H, d), 7.59(1H, s), 8.59(1H, s).

REFERENTIAL EXAMPLE 3

1-Cyclopropyl-4-thiopyridone (a) 4.5 g of pyran-4-one was dissolved in 100 ml of benzene, and 10.6 g of Lawesson's reagent (2,4-bis(4-methoxyphenyl)-1,3-dithia-2,4-diphosphethane-2,4-disulfide) was added thereto and stirred for 30 minutes at 80° C. After cooling, the insoluble part was filtrated out, and the remaining filtrate solution was concentrated and then subjected to silicagel-column chromatography (250 g, toluene/ethyl acetate=5/1) to obtain 5.18 g (98%) of pyran-4-thione.

NMR(CDCl$_3$) δ: 7.14(2H,d), 7.48(2H,d).

(b) 1.12 g of pyran-4-thione was dissolved in 20 ml of ethanol, and 1.05 ml of cyclopropylamine was added thereto, while cooled with ice, and reacted for 15 minutes at room temperature. After the reaction, the reaction solution was concentrated and the remaining residue was subjected to silicagel-column chromatography (chloroform/methanol=20/1) to obtain 1.32 g of a crystal, which is the above-entitled compound.

NMR(CDCl$_3$) δ: 1.08(2H, m), 1.17(2H, m), 3.49(1H, m), 7.27(2H, d), 7.38(2H, d).

REFERENTIAL EXAMPLE 4

1-(2-Hydroxyethyl)-4-thiopyridone

In the same manner as the Referential Example 3(b), with the exception that ethanolamine was used, the above-entitled compound was obtained.

NMR(D$_2$O) δ: 4.12(2H, m), 4.42(2H, m), 7.69(2H, d) 7.95(2H, d).

REFERENTIAL EXAMPLE 5

1-(2-Dimethylaminoethyl)-4-thiopyridone

In the same manner as the Referential Example 3(b), with the exception that N,N-dimethylethylenediamine was used, the above-entitled compound was obtained.

NMR(CDCl$_3$) δ:2.24(6h, s), 2.65(2H, t), 3.96(2H, t), 7.25(2H, d), 7.42(2H, d).

REFERENTIAL EXAMPLE 6

1-(2-Fluoroethyl)-4-thiopyridone 1.12 g of pyran-4-thione was dissolved in 20 ml of ethanol and 10 ml of pyridine, and 2 g of 2-fluoroethylamine hydrochloride was added thereto and reacted for 3 hours at 60° C. The reaction solution was concentrated, and then chloroform was added thereto and the insoluble part was filtrated out. The remaining filtrate solution was concentrated to a small amount and purified by means of silicagel-column chromatography (chloroform/methanol=20/1), to obtain 890 mg of the above-entitled compound.

NMR(CDCl$_3$) δ: 4.17(2H, tt), 4.73(2H, tt), 7.18(2H, d) 7.42(2H, d).

REFERENTIAL EXAMPLE 7

1-(2-Sulfoethyl)-4-thiopyridone 1.12 g of pyran-4-thione was dissolved in 20 ml of ethanol, and 1.25 g of 2-aminoethanesulfonic acid and 10 ml of 1N-NaOH were added thereto and reacted for 1.5 hours at 70° C. After the reaction, ethanol was removed off, and the remaining reaction solution was purified with HP-20 column-chromatography to obtain 2.1 g of the above-entitled compound (in the form of sodium salt).

NMR(D$_2$O) δ: 3.46(2H, t), 4.57(2H, t), 7.56(2H, d), 7.88(2H, d).

REFERENTIAL EXAMPLE 8

1-(2-Sulfamoylethyl)-4-thiopyridone 1.12 g of pyrane-4-thione was dissolved in 10 ml of ethanol, and a solution obtained by dissolving 2.48 g of 2-sulfamoylethylamine in a mixture comprising 10 ml of ethanol and 5 ml of water was added dropwise thereto. These were reacted at room temperature for 1 hour and then at 50°-60° C. for about 1.5 hours. After the reaction, the reaction solution was concentrated to dryness, and the residue formed was washed with methylene chloride. 30 ml of water was added to the residue and the crystal as precipitated was taken out by filtration, while cooled, and thereafter washed with water and then with ether and dried to obtain 490 mg of the above-entitled compound.

NMR(DMSO-d$_6$) δ: 3.52(2H, t), 4.35(2H, t), 7.08(2H, br.s), 7.14(2H, d), 7.63(2H, d).

REFERENTIAL EXAMPLE 9

1-Carboxymethyl-4-thiopyridone (a) 14.25 g of 4-pyridone was dissolved in 250 ml of DMF, and 25 ml of ethyl bromoacetate and 31.1 g of potassium carbonate were added thereto and reacted for 2.5 hours at 60° C. After the reaction, the insoluble part was filtrated out, and the remaining filtrate solution was concentrated. The formed residue was purified with silicagel-column chromatography (chloroform/methanol=10/1-5/1), to obtain 22.8 g of 1-ethoxycarbonylmethyl-4-pyridone. This was dissolved in 400 ml of dimethoxyethane and 30 g of Lawesson's reagent was added thereto and reacted for 30 minutes, while heated under reflux. After the reaction, the reaction solution was concentrated, and the residue formed was purified with silicagel-column chromatography (chloroform/methanol=20/1) and then crystallized with dichloromethane/ether, to obtain 13.6 g of 1-ethoxycarbonylmethyl-4-thiopyridone.

NMR(CDCl$_3$) δ: 1.32(3H, t), 4.29(2H, q), 4.65(2H, s), 7.13(2H, d), 7.37(2H, d).

(b) 9.6 g of 1-ethoxycarobnylmethyl-4-thiopyridone was dissolved in 120 ml of ethanol, and 68 ml of 1N-NaOH was added thereto and reacted for 20 minutes at room temperature. After the reaction, the reaction solution was concentrated to remove ethanol therefrom, and 68 ml of 1N HCl was added thereto, while cooled with ice, and the precipitate formed was taken out by filtration and dried to obtain 5.23 g of the above-entitled compound.

NMR(DMSO-d$_6$) δ: 4.86(2H, s), 7.18(2H, d), 7.55(2H, d)

REFERENTIAL EXAMPLE 10

1-Carbamoylmethyl-4-thiopyridone 1.57 g of 1-ethoxycarbonylmethyl-4-thiopyridone was added to 15 ml of concentrated aqueous ammonia, while cooled with ice, and reacted for 1 hour. The reaction solution was concentrated to drying under reduced pressure, and water was added thereto and the precipitate formed was taken out by filtration. After washed with water and dried, 980 mg of the above-entitled compound was obtained.

NMR(DMSO-d$_6$) δ: 4.70(2H, s), 7.16(2H, d), 7.42(1H, s), 7.50(2H, d), 7.84(1H, s).

REFERENTIAL EXAMPLE 11

1-Hydroxyaminocarbonylmethyl-4-thiopyridone 200 mg of hydroxylamine was dissolved in 15 ml of ethanol, and 1.25 g of 1-ethoxycarbonylmethyl-4-thiopyridone was added thereto and reacted for 24 hours at room temperature. After cooling with ice, the precipitate formed was taken out by filtration, washed with ethanol and dried to obtain 660 mg of the above-entitled compound.

NMR(DMSO-d$_6$) δ: 4.62(2H, s), 7.18(2H, d), 7.50(2H, d).

REFERENTIAL EXAMPLE 12

1-(2-Hydroxyethyl)-3-mercapto pyridinium chloride 5.3 g of 3-benzoylthiopyridine was dissolved in 30 ml of acetone, and 9.4 ml of 2-iodoethanol was added thereto and reacted for 16 hours, while heated under reflux. After the reaction, the reaction solution was concentrated and the remaining residue was washed with ether and then with a mixture solution of methylene chloride/ether (=2/1) and dried to obtain 5.3 g of 1-hydroxyethyl-3-benzoylthiopyridinium iodide.

2.58 g of the product as obtained above was dissolved in 35 ml of 6N-HCl and reacted for 1 hour, while heated under reflux. After the reaction, the reaction solution was concentrated to drying, and the solid formed was dissolved in 20 ml of water and purified with IR-120 (H$^+$, 40 ml) column-chromatography, to obtain 1.17 g of the above-entitled compound from the eluate with 3N-HCl.

NMR(D$_2$O) δ: 4.03(2H, t), 4.63(2H, t), 7.87(1H, dd), 8.43(1H, d), 8.57(1H, d), 8.79(1H, s).

REFERENTIAL EXAMPLE 13

2,3-Dihydro-5(1H)-indolidinethione 720 mg of 2,3-dihydro-6,7-bis(trimethylsilyl)-5(1H)-indolidinone (as described in "Journal of Organic Chemistry", vol. 49, p. 4786, in 1984) was stirred in 85 ml of 1M tetrabutylammonium fluoride solution in THF, for 30 minutes at 60° C. A little amount of water was added thereto and the whole was concentrated under reduced pressure, and then, after water was added thereto, this was extracted with ether. The ether layer as extracted was washed with water and dehydrated with magnesium sulfate and ether was distilled out. The residue obtained was subjected to column-chromatography with SiO$_2$ (30 g) and to elution with ethyl acetate, to obtain 640 mg of 2,3-dihydro-6-trimethylsilyl-5(1H)-indolidinone. Next, this was dissolved in 5 ml of benzene and 5 ml of trifluoroacetic acid was added thereto and stirred for 1 hour at 60° C. The reaction solution was concentrated and ethyl acetate was added thereto, and then extracted with NaHCO$_3$-aqueous solution and water. The separated aqueous layer was extracted with chloroform and dehydrated with magnesium sulfate. Chloroform was distilled out and the residue was subjected to column-chromatography with SiO$_2$ (20 g). After elution with chloroform/methanol (20/1), 183 mg (53%) of 2,3-dihydro-5(1H)-indolidinone was obtained. 168 mg of this product was dissolved in 5 ml of benzene, and 311 mg of Lawesson's reagent was added thereto and heated for 2 hours under reflux. After cooling, chloroform was added to dissolve the precipitate, and the resulting solution was then concentrated. The residue formed was subjected to column-chromatography with SiO$_2$ (20 g, chloroform/methanol=50/1) twice, to obtain 167 mg (89%) of the above-entitled compound.

NMR(CDCl$_3$) δ: 2.22(2H, tt), 3.20(2H, t), 4.58(2H, t), 6.55(1H, d), 7.16(1H, t), 7.43(1H, t).

EXAMPLE 1

(6R,7R)7-[(RS)2-(2-Aminothiazol-4-yl)-2-(1,5-dihydroxy-4-pyridone-2-carboxamido)actamido]-3-acetoxymethyl-ceph-3-em-4-carboxylic acid (Method A)

(a) 780 mg of 5-benzyloxy-1-hydroxy-4-pyridone-2-carboxylic acid was suspended in 12 ml of tetrahydrofuran, and 0.54 ml of triethylamine was added thereto and dissolved.

624 mg of phosphorus pentachloride was added thereto at −15° C. and reacted for 1 hour. On the other hand, 920 mg of (6R,7R)7-[(RS)2-(2-aminothiazol-4-yl)-2-aminoacetamido]-3-acetoxymethyl-ceph-3-em-4-carboxylic acid hydrochloride was dissolved in 30 ml of 50%-tetrahydrofuran aqueous solution, and triethylamine was added thereto, while cooled with ice, to regulate the pH value thereof to 8.

To this was added the previously formed tetrahydrofuran solution little by little, while the pH value of the reaction solution was kept to be 8–8.5 with triethylamine. After the reaction, the reaction solution was regulated to have pH of 6.5, and then concentrated under reduced pressure to remove tetrahydrofuran therefrom. Afterwards, water was added to the remaining residue and the resulting solution was regulated to have a pH of 2 with 1N-HCl while cooled with ice. The precipitate formed was taken out by filtration and dried to obtain 1.25 g of crude powder of (6R,7R)7-[(RS)2-(2-aminothiazol-4-yl)-2-(5-benzyloxy-1-hydroxy-4-pyridone-2-carboxamido)acetamido]-3-acetoxymethyl-ceph-3-em-4-carboxylic acid. This was suspended in 20 ml of 50%-methanol and then dissolved wth saturated aqueous NaHCO$_3$, while the pH of the solution was regulated to be 6.5–7.0 and thereafter purified with LH-20 column-chromatography (50%-methanol/water) to obtain 500 mg of sodium (6R,7R)7-[(RS)2-(2-aminothiazol-4-yl)-2-(5-benzyloxy-1-hydroxy-4-pyridone-2-carboxamido)acetamido]-3-acetoxymethyl-ceph-3-em-4-carboxylate.

(b) Next, the above obtained product was added to 30 ml of aqueous water containing 500 mg of palladium-black, and acetic acid was added thereto to adjust the pH value thereof to 5, and was subjected to catalytic hydrogenation at room temperature under atmospheric pressure. After the reduction, the palladium-black was filtrated out and the reaction solution was concentrated to a small amount and then was regulated to have a pH of 7.0. This was purified with HP-20 column-chromatography (for elution with H$_2$O to 5% acetone/H$_2$O) and 250 mg of the above-entitled compound was obtained in the form of sodium salt.

NMR (D$_2$O) δ 2.11, 2.12 (each 3/2H, s), 3.48($\frac{1}{2}$×2H, ABq), 3.55($\frac{1}{2}$×2H, ABq), 4.79($\frac{1}{2}$×2H, ABq), 4.82($\frac{1}{2}$×2H, ABq), 5.11($\frac{1}{2}$H, d), 5.15($\frac{1}{2}$H, d), 5.60($\frac{1}{2}$H, s), 5.62($\frac{1}{2}$H, s), 5.65($\frac{1}{2}$H, d), 5.75($\frac{1}{2}$H, d), 6.75($\frac{1}{2}$H, s), 6.80($\frac{1}{2}$H, s), 7.48(1H, s), 7.60(1H, s).

(Method B)

(a) 7.1 g of 5-p-methoxybenzyloxy-1-hydroxy-4-pyridone-2-carboxylic acid was suspended in 100 ml of tetrahydrofuran, and 4.4 ml of triethylamine was added thereto and dissolved. Next, 5.33 g of phosphorus pentachloride was added thereto, as divided into four times, at −10° or −15° C., and reacted at the same temperature for 1 hour, to obtain an acid chloride solution.

On the other hand, 11.9 g of soidum syn-7-[2-(2-aminothiazol-4-yl)-2-methoxyiminoacetamido]-3-acetoxymethyl-ceph-3-em-4-carboxylate was dissolved in 250 ml of formic acid and 20 ml of water, and 11 g of zinc powder was added thereto little by little, while cooled with ice. After reaction for 30 minutes, the zinc powder was filtrated out, and the remaining filtrate was, after washed with formic acid, concentrated under reduced pressure. 250 ml of water was added to the residue, and hydrogen sulfide gas was introduced thereinto for 10 minutes, while cooled with ice, and the precipitate formed was filtrated out. The remaining filtrate solution was concentrated under reduced pressure and then water was added thereto to make 200 ml in all. Next, 100 ml of tetrahydrofuran was added thereto to obtain (6R,7R)7-[(RS)2-(2-aminothiazol-4-yl)-2-aminoacetamido]-3-acetoxymethyl-ceph-3-em-4-carboxylic acid solution.

Triethylamine was added to the obtained solution, while cooled with ice, and the previously prepared acid chloride solution was added thereto, while the pH value of the solution was kept to 8–8.5, and reacted for 1 hour.

After the reaction, tetrahydrofuran was removed off under reduced pressure, and the pH value of the solution was made to be 2 with 6N-HCl, while cooled with ice, and thus, the precipitate formed was taken out by filtration, washed with water and dried to obtain 9.2 g of a crude powder of (6R,7R)7-[(RS)2-(2-aminothiazol-4-yl)-2-(5-p-methoxybenzyloxy-1-hydroxy-4-pyridone-2-carboxamido)acetamido]-3-acetoxymethyl-ceph-3-em-4-carboxylic acid.

(b) The product obtained above was suspended in 22 ml of anisole, and 97 ml of trifluoroacetic acid was added dropwise thereto, while cooled with ice, and reacted for 30 minutes at room temperature. Afterwards, the reaction mixture was dropped into 700 ml of diisopropylether.

The precipitate formed was taken out by filtration, washed with diisopropylether and dried. The precipitate obtained was dissolved in about 60 ml of saturated sodium hydrogencarbonate aqueous solution (pH 7.2–7.4) and purified with HP-20 column-chromatography, to obtain 3.34 g of the above entitled compound in the form of sodium salt. The spectral data of the compound obtained were the same as those of the same compound obtained by the Method A in the above.

(Method C)

171 mg of 1,5-dihydroxy-4-pyridone-2-carboxylic acid was suspended in 5 ml of tetrahydrofuran, and 0.18 ml of triethylamine and 208 mg of phosphorus pentachloride were added thereto, while cooled with ice, and reacted for 1 hour at room temperature. On the other hand, 300 mg of (6R,7R)7-[(RS)2-(2-aminothiazol-4-yl)-2-aminoacetamido]-3-acetoxymethyl-ceph-3-em-4-carboxylic acid hydrochloride was dissolved in 10 ml of 50%-tetrahydrofuran aqueous solution, and the solution was regulated to have pH of 7.5 with saturated NaHCO$_3$ aqueous solution. To this was added the previously prepared tetrahydrofuran solution little by little, while this was cooled with ice and the pH of the reaction solution was regulated to be 8.0. After the reaction, the pH of the reaction solution was regulated to be 6.0, and the solution was concentrated under reduced pressure to remove tetrahydrofuran therefrom. The remaining aqueous solution was regulated to have a pH of 2.0 with 1N-HCl, and the precipitate formed was taken out by filtration and dried, and then this was purified with HP-20 and LH-20 column chromatography, in the same manner as mentioned above, to obtain 60 mg of sodium salt of the above-entitled compound. The spectral data of the compound obtained were the same as those of the same compound obtained by the Method A in the above.

EXAMPLE 2

(6R,7R)7-[(RS)2-(2-Aminothiazol-4-yl)-2-(1,5-dihydroxy-4-pyridone-2-carboxamido)acetamido]-3-(1-methylpyridinium-4-yl)thiomethyl-ceph-3-em-4-carboxylate 960 mg of sodium (6R,7R)7-[(RS)2-(2-aminothiazol-4-yl)-2-(1,5-dihydroxy-4-pyridone-2-carboxamido)acetamido]-3-acetoxymethyl-ceph-3-em-4-carboxylate (as obtained in the above Example 1) was dissolved in 8 ml of acetonitrile and 8 ml of water, and 2.5 g of sodium iodide and 360 mg of 1-methyl-4-thiopyridone were added thereto and, after the pH of the reaction solution was adjusted to 6.8, reacted for 4.5 hours at 65°–70° C. After the reaction, the reaction solution was added dropwise to 200 ml of acetone, and the precipitate formed was taken out by filtration. After washed with acetone and dried, the obtained precipitate was dissolved in 15 ml of water and then purified with HP-20 column chromatography (development solvent: 5% acetone aqueous solution), to obtain 380 mg of the above-entitled product. This was further purified with LH-20 column chromatography (50% methanol aqueous solution), to obtain 230 mg of the product.

NMR(D$_2$O) δ: 3.54(½×2H, ABq), 3.58(½×2H, ABq), 4.29(½×2H, ABq), 4.32(½×2H, ABq), 4.22(3H, s), 5.09(½H, d), 5.13(½H, d), 5.62(1H, s), 5.62(½H, d), 5.73(½H, d), 6.76(½H, s), 6.81(½H, s), 7.39(½H, s), 7.40(½H, s), 7.63(½H, s), 7.64(½H, s), 7.81(2H, d), 8.40(2H, d).

In the same manner as the Example 2, with the exception that the reagent of (A) as given below was used instead of 1-methyl-4-thiopyridone, products of the following Examples 3 through 39 were obtained.

EXAMPLE 3

(6R,7R)7-[(RS)2-(2-Aminothiazol-4-yl)-2-(1,5-dihydroxy-4-pyridone-2-carboxamido)acetamido]-3-(1-carboxymethylpyridinium-4-yl)thiomethyl-ceph-3-em-4-carboxylate (A): 1-Carboxymethyl-4-thiopyridone NMR(D$_2$O) δ: 3.38(½H, d), 3.43(½H, d), 3.66(½H, d), 3.70(½H, d), 4.15(½H, d), 4.17(½H, d), 4.40(½H, d), 4.43(½H, d), 5.06(2H, s), 5.08(½H, d), 5.11(½H, d), 5.62(1H, s), 5.63(½H, d), 5.73(½H, d), 6.74(½H, s), 6.78(½H, s), 7.40(1H, s), 7.66(1H, s), 7.81(2H, d), 8.37(2H, d).

EXAMPLE 4

(6R,7R)7-[(RS)2-(2-Aminothiazol-4-yl)-2-(1,5-dihydroxy-4-pyridone-2-carboxamido)acetamido]-3-(1-methylpyridinium-3-yl)thiomethyl-ceph-3-em-4-carboxylate (A): 3-Mercapto-1-methylpyridinium chloride NMR(D$_2$O) δ: 3.38(½H, d), 3.43(½H, d), 3.62(½H, d), 3.64(½H, d), 3.96(½H, d), 3.99(½H, d), 4.19(1H, d), 4.30(3/2H, s), 4.31(3/2H, s), 5.01(½H, d), 5.04(½H, d), 5.51(½H, d), 5.58(½H, s), 5.59(½H, s), 5.60(½H, d), 6.69(½H, s), 6.74(½H, s), 7.33(1H, s), 7.57(½H, s), 7.58(½H, s), 7.85(1H, m), 8.37(1H, m), 8.57(1H, d), 8.85(1H, s).

EXAMPLE 5

(6R,7R)7-[(RS)2-(2-Aminothiazol-4-yl)-2-(1,5-dihydroxy-4-pyridone-2-carboxamido)acetamido]-3-[1-(2-hydoroxyethyl)pyridinium-4-yl]thiomethyl-ceph-3-em-4-carboxylate (A) 1-(2-Hydroxyethyl)-4-thiopyridone NMR(D$_2$O) δ: 3.37(½H, d), 3.43(½H, d), 3.63(½H, d), 3.68(½H, d), 4.01(2H, t), 4.14(½H, d), 4.17(½H, d), 4.37(½H, d), 4.40(½H, d), 4.53(2H, m), 5.07(½H, d), 5.11(½H, d), 5.60(1H, s), 5.61(½H, d), 5.70(½H, d), 6.73(½H, s), 6.77(½H, s), 7.29(½H, s), 7.30(½H, s), 7.52(½H, s), 7.54(½H, s), 7.79(2H, m), 8.43(2H, m).

EXAMPLE 6

(6R,7R)7-[(RS)2-(2-Aminothiazol-4-yl)-2-(1,5-dihydroxy-4-pyridone-2-carboxamido)acetamido]-3-(1-carbamoylmethylpyridinium-4-yl)thiomethyl-ceph-3-em-4-carboxylate (A); 1-Carbamoylmethyl-4-thiopyridone NMR(D$_2$O) δ: 3.40(½H, d), 3.45(½H, d), 3.65(½H, d), 3.71(½H, d), 4.17(½H, d), 4.22(½H, d), 4.41(½H, d), 4.45(½H, d), 5.08(½H, d), 5.11(½H, d), 5.33(2H, br.s.), 5.61(½H, d), 5.61(1H, s), 5.71(½H, d), 6.74(½H, s), 6.79(½H, s), 7.37(1H, s), 7.59(½H, s), 7.60(½H, s), 7.85(2H, m), 8.40(2H, m).

EXAMPLE 7

(6R,7R)7-[(RS)2-(2-Aminothiazol-4-yl)-2-(1,5-dihydroxy-4-pyridone-2-carboxamido)acetoamido]-3-[1-(2-dimethylaminoethyl)pyridinium-4-yl]thiomethyl-ceph-3-em-4-carboxylate (A): 1-(2-Dimethylaminoethyl)-4-thiopyridone
NMR(D$_2$O) δ: 2.47(3H, s), 2.50(3H, s), 3.20(2H, m), 3.37(½H, d), 3.41(½H, d), 3.64(½H, d), 3.68(½H, d), 4.14(1H, d), 4.38(1H, d), 4.65(2H, m), 5.08(½H, d), 5.12(½H, d), 5.60(½H, d), 5.61(1H, s), 5.71(½H, d), 6.72(½H, s), 6.77(½H, s), 7.31(½H, s), 7.35(½H, s), 7.54(½H, s), 7.58(½H, s), 7.82(2H, m), 8.47(2H, m).

EXAMPLE 8

(6R,7R)7-[(RS)2-(2-Aminothiazol-4-yl)-2-(1,5-dihydroxy-4-pyridone-2-carboxamido)acetamido]-3-(1-cyploroylpyridinium-4-yl)thiomethyl-ceph-3-em-4-carboxylate (A): 1-Cyclopropyl-4-thiopyridone
NMR(D$_2$O) δ: 1.30(4H, m), 3.36(½H, d), 3.42(½H, d), 3.63(½H, d), 3.67(½H, d), 4.15(2H, m), 4.38(½H, d), 4.42(½H, d), 5.05(½H, d), 5.09(½H, d), 5.57(1H, s), 5.58(½H, d), 5.68(½H, d), 6.73(½H, s), 6.77(½H, s), 7.37(½H, s), 7.38(½H, s), 7.59(½H, s), 7.60(½H, s), 7.76(2H, m), 8.52(2H, d).

EXAMPLE 9

(6R,7R)7-[(RS)2-(2-Aminothiazol-4-yl)-2-(1,5-dihydroxy-4-pyridone-2-carboxamido)acetamido]-3-(1-hydroxyaminocarbonylmethylpyridinium-4-yl)thiomethyl-ceph-3-em-4-carboxylate (A): 1-Hydroxyaminocarbonylmethyl-4-thiopyridone
NMR(D$_2$O) δ: 3.41(½H, d), 3.46(½H, d), 3.69(½H, d), 3.73(½H, d), 4.17(½H, d), 4.20(½H, d), 4.43(½H, d), 4.47(½H, d), 5.06(2H, s), 5.10(½H, d), 5.14(½H, d), 5.61(1H, s), 5.61(½H, d), 5.73(½H, d), 6.76(½H, s), 6.80(½H, s), 7.43(1H, s), 7.68(1H, s), 7.83(2H, m), 8.39(2H, d).

EXAMPLE 10

(6R,7R)7-[(RS)2-(2-Aminothiazol-4-yl)-2-(1,5-dihydroxy-4-pyridone-2-carboxamido)acetamido]-3-[1-(2-fluoroethyl)pyridinium-4-yl]thiomethyl-ceph-3-em-4-carboxylate (A): 1-(2-Fluoroethyl)-4-thiopyridone
NMR(D$_2$O) δ: 3.37(½H, d), 3.43(½H, d), 3.65(½H, d), 3.68(½H, d), 4.13(½H, d), 4.17(½H, d), 4.42(½H, d), 4.45(½H, d), 4.7–4.95(4H, m), 5.05(½H, d), 5.10(½H, d), 5.57(1H, s), 5.58(½H, d), 5.68(½H, d), 6.73(½H, s), 6.78(½H, s), 7.38(1H, s), 7.62(1H, s), 7.87(2H, m), 8.48(2H, d).

EXAMPLE 11

(6R,7R)7-[(RS)2-(2-Aminothiazol-4-yl)-2-(1,5-dihydroxy-4-pyridone-2-carboxamido)acetamido]-3-[1-(2-hydroxyethyl)pyridinium-3-yl]thiomethyl-ceph-3-em-4-carboxylate (A): 1-(2-Hydroxyethyl)-3-mercaptopyridinium chloride
NMR(D$_2$O) δ: 3.40(½H, d), 3.47(½H, d), 3.70(½H, d), 3.71(½H, d), 4.03(2H, m), 4.10(2H, ABq), 4.65(2H, m), 5.04(½H, d), 5.07(½H, d), 5.50(½H, d), 5.58(1H, s), 5.61(½H, d), 6.71(½H, s), 6.76(½H, s), 7.37(½H, s), 7.38(½H, s), 7.60(1H, s), 7.94(1H, m), 8.50(1H, m), 8.68(1H, m), 8.99(1H, br.s.).

EXAMPLE 12

(6R,7R)7-[(RS)2-(2-Aminothiazol-4-yl)-2-(1,5-dihydroxy-4-pyridone-2-carboxamido)acetamido]-3-[1-(2-sulfoethyl)pyridinium-4-yl]thiomethyl-ceph-3-em-4-carboxylate (A): 1-Sulfoethyl)-4-thiopyridone
NMR(D$_2$O) δ: 3.36(½H, d), 3.42(½H, d), 3.54(2H, t), 3.64(½H, d), 3.68(½H, d), 4.13(½H, d), 4.15(½H, d), 4.37(½H, d), 4.41(½H, d), 4.82(2H, m), 5.07(½H, d), 5.10(½H, d), 5.58(½H, s), 5.59(½H, s), 5.61(½H, d), 5.70(½H, d), 6.73(½H, s), 6.77(½H, s), 7.38(178 H, s), 7.39(½H, s), 7.62(½H, s), 7.63(½H, s), 7.78(1H, d), 7.80(1H, d), 8.49(1H, d), 8.51(1H, d).

EXAMPLE 13

(6R,7R)7-[(RS)2-(2-Aminothiazol-4-yl)-2-(1,5-dihydroxy-4-pyridone-2-carboxamido)acetamido]-3-[1-(2-sulfamoylethyl)pyridinium-4-yl]thiomethyl-ceph-3-em-4-carboxylate (A): 1-(2-Sulfamoylethyl)-4-thiopyridone
NMR(D$_2$O) δ: 3.35(½H, d), 3.39(½H, d), 3.60(½H, d), 3.67(½H, d), 3.93(2H, t), 4.17(½H, d), 4.18(½H, d), 4.34(½H, d), 4.38(½H, d), 4.92(2H, br.s), 5.06(½H, d), 5.09(½H, d), 5.59(½H, s), 5.59(½H, s), 5.60(½H, d), 5.69(½H, d), 6.71(½H, s), 6.75(½H, s), 7.35(½H, s), 7.36(½H, s), 7.59(½H, s), 7.60(½H, s), 7.80(1H, d), 7.81(1H, d), 8.51(2H, d).

EXAMPLE 14

(6R,7R)7-[(RS)2-(2-Aminothiazol-4yl)-2-(1,5-dihydroxy-4-pyridone-2-carboxamido)acetamido]-3-(2,3-cyclopenteno-1-methylpyridinium-4-yl)-thiomethyl-ceph-3-em-4-carboxylate (A): 1-Methylcyclopentano[b]4-thiopyridone
NMR(D$_2$O) δ: 2.28(2H, m), 3.88(2H, m), 3.21(2H, m), 3.55(½×2H, ABq), 3.60(½×2H, ABq), 4.04(3H, s), 4.26(½×2H, ABq), 4.28(½×2H, ABq), 5.09(½H, d), 5.13(½H, d), 5.62(½H, d), 5.63(1H, s), 5.72(½H, d), 6.75(½H, s), 6.79(½H, s), 7.26(½H, s), 7.31(½H, s), 7.53(1H, d), 7.54((½H, s), 7.57(½H, s), 8.15(1H, d).

EXAMPLE 15

(6R,7R)7-[(RS)2-(2-Aminothiazol-4-yl)-2-(1,5-dihydroxy-4-pyridone-3-carboxamido)acetamido]-3-(2,3-cyclopentenopyridine-4-yl)thiomethyl-ceph-3-em-4-carboxylic acid (A): Cyclopentano[b]4-thiopyridone
NMR(D$_2$O) δ: 2.16(2H, m), 2.82(2H, m), 3.01(2H, m), 3.49(½×2H, ABq), 3.55(½×2H, ABq), 4.17(½×2H, ABq), 4.20(½×2H, ABq), 5.02(½H, d), 5.07(½H, d), 5.60(½H, d), 5.62(1H, s), 5.70(½H, d), 6.75(½H, s), 6.80(½H, s), 7.21(1H, d), 7.37(½H, s), 7.39(½H, s), 7.61(½H, s), 7.62(½H, s), 8.12(1H, d).

EXAMPLE 16

(6R,7R)7-[(RS)2-(2-Aminothiazol-4-yl)-2-(1,5-dihydroxy-4-pyridone-2-carboxamido)acetamido]-3-(pyridine-4-yl)thiomethyl-ceph-3-em-4-carboxylic acid (A): 4-Mercaptopyridine
NMR(D$_2$O) δ: 3.50(½×2H, ABq), 3.57(½×2H, ABq), 4.15(½×2H, ABq), 4.17(½×2H, ABq), 5.01(½H, d), 5.05(½H, d), 5.58(½H, d), 5.60(1H, s), 5.67(½H, d), 6.74(½H, s), 6.79(½H, s), 7.40(2H, d), 7.42(1H, s), 7.62(1H, s), 8.33(2H, d).

EXAMPLE 17

(6R,7R)7-[(RS)2-(2-Aminothiazol-4-yl)-2-(1,5-dihydroxy-4-pyridone-2-carboxamido)acetamido]-3-(2,3-cyclopenteno-1-carboxylmethylpyridinium-4-yl)-thiomethyl-ceph-3-em-4-carboxylate (A): 1-Carboxymethyl-cyclopentano[b]4-thiopyridone NMR(D$_2$) δ: 2.30(2H, m), 2.98(2H, m), 3.17(2H, m), 3.53(½×2H, ABq), 3.58(½×2H, ABq), 4.30(½×2H, ABq), 4.32(½×2H, ABq), 4.94(2H, s), 5.06(½H, d), 5.10(½H, d), 5.60(1H, s), 5.61(½H, d), 5.71(½H, d), 6.75(½H, s), 6.79(½H, s), 7.40(½H, s), 7.41(½H, s), 7.60(1H, m), 7.65(½H, s), 7.66(½H, s), 8.18(1H, m).

EXAMPLE 18

(6R,7R)7-[(RS)2-(2-Aminothiazol-4-yl)-2-(1,5-dihydroxy-4-pyridone-2-carboxamido)acetamido]-3-(2,3-cyclopentenopyridinium)methyl-ceph-3-em-4-carboxylate (A): 2,3-Cyclopentenopyridine NMR(D$_2$O) δ: 2.33(2H, m), 3.20(3H, m), 3.35(2H, m), 3.45(½H, d), 3.48(½H, d), 5.15(½H, d), 5.18(½H, d), 5.32(1H, m), 5.48(1H, m), 5.61(1H, s), 5.68(½H, d), 5.78(½H, d), 6.75(½H, s), 6.79(½H, s), 7.43(1H, s), 7.69(½H, s), 7.70(½H, s), 7.80(1H, m), 8.30(1H, m), 8.53(½H, d), 8.56(½H, d).

EXAMPLE 19

(6R,7R)7-[(RS)2-(2-Aminothiazol-4-yl)-2-(1,5-dihydroxy-4-pyridone-2-carboxamido)acetamido]-3-(2,3-cyclopenteno-4-methylthiopyridinium)methyl-ceph-3-em-4-carboxylate (A): 2,3-Cyclopenteno-4-methylthiopyridine NMR(D$_2$O) δ: 2.33(2H, m), 2.68(3/2H, s), 2.69(3/2H, s), 2.95(2H, m), 3.27(2H, m), 3.15–3.50(2H, m), 5.15(½H, d), 5.18(½H, d), 5.10–5.35(2H, m), 5.60(1H, s), 5.67(½H, d), 5.78(½H, d), 6.75(½H, s), 6.79(½H, s), 7.37(1H, s), 7.50(½H, d), 7.52(½H, d), 7.62(1H, s), 8.32(½H, d), 8.34(½H, d).

EXAMPLE 20

(6R,7R)7-[(RS)2-(2-Aminothiazol-4-yl)-2-(1,5-dihydroxy-4-pyridone-2-carboxamido)acetamido]-3-(4-methylthiopyridinium)methyl-ceph-3-em-4-carboxylate (A): 4-Methylthiopyridine NMR(D$_2$O) δ: 2.62(3/2H, s), 2.64(3/2H, s), 3.35(½×2H, ABq), 3.40(½×2H, ABq), 5.10(1H, m), 5.18(½H, d), 5.20(½H, d), 5.36(1H, m), 5.57(½H, s), 5.58(½H, s), 5.67(½H, d), 5.78(½H, d), 6.70(½H, s), 6.74(½H, s), 7.33(1H, s), 7.60(1H, s), 7.70(1H, d), 7.74(1H, d), 8.53(2H, m).

EXAMPLE 21

(6R,7R)7-[(RS)2-(2-Aminothiazol-4-yl)-2-(1,5-dihydroxy-4-pyridone-2-carboxamido)acetamido]-3-(1-methyl-1H-tetrazol-5-yl)thiomethyl-ceph-3-em-4-carboxylic acid (A): 5-Mercapto-1-methyl-1H-tetrazole NMR(D$_2$O) δ: 7.64(1H, s), 7.40(1H, s), 6.81(½H, s), 6.76(½H, s), 5.71(½H, d), 5.62(½H, d), 5.63(½H, s), 5.61(½H, s), 5.12(½H, d), 5.09(½H, d), 4.35(½H, d), 4.32(½H, d), 4.07(3/2H, s), 4.05(3/2H, s), 4.05(1H, m), 3.78(½H, d), 3.74(½H, d), 3.47(½H, d), 3.41(½H, d).

EXAMPLE 22

(6R,7R)7-[(RS)2-(2-Aminothaizol-4-yl)-2-(1,5-dihydroxy-4-pyridone-2-carboxamido)acetamido]-3-(4,5-dihydro-4-methyl-5-oxo-6-hydroxy-1,2,4-triazin-3-yl)thiomethyl-ceph-3-em-4-carboxylic acid (A): 4,5-Dihydro-3-mercapto-4-methyl-5-oxo-6-hydroxy-1,2,4-triazine NMR(D$_2$O) δ: 7.64(1H, s), 7.40(1H, s), 6.80(½H, s), 6.75(½H, s), 5.72(½H, d), 5.63(3/2H, m), 5.10(½H, d), 5.07(½H, d), 4.50(½H, d), 4.48(½H, d), 3.80(2H, m), 3.47(3/2H, s), 3.45(3/2H, s), 3.41(½H, d), 3.35(½H, d).

EXAMPLE 23

(6R,7R)7-[(RS)-2-(2-Aminothiazol-4-yl)-2-(1,5-dihydroxy-4-pyridone-2-carboxamido)acetamido]-3-(1-amino-1H-tetrazol-5-yl)thiomethyl-ceph-3-em-4-carboxylic acid (A): 5-Mercapto-1-amino-1H-tetrazole NMR(D$_2$O) δ: 7.61(1H, s), 7.38(1H, s), 6.81(½H, s), 6.76(½H, s), 5.75(½H, d), 5.65(½H, d) 5.61(½H, s), 5.59(½H, s), 5.17(½H, d), 5.13(½H, d), 4.12(1H, s), 4.10(1H, s), 3.68(½H, d), 3.63(½H, d), 3.41(½H, d), 3.37(½H, d).

EXAMPLE 24

(6R,7R)7-[(RS)2-(2-Aminothiazol-4-yl)-2-(1,5-dihydroxy-4-pyridone-2-carboxamido)acetamido]-3-[1-(2-dimethylaminoethyl)-1H-tetrazol-5-yl]thiomethyl-ceph-3-em-4-carboxylic acid (A): 5-Mercapto-1-(2-dimethylaminoethyl)-1H-tetrazole NMR(D$_2$O) δ: 7.63(1H, s), 7.41(1H, s), 6.81(½H, s), 6.75(½H, s), 5.69(½H, d), 5.61(1H, s), 5.58(½H, d), 5.13(½H, d), 5.10(½H, d), 4.80(2H, m), 4.28(½H, d), 4.27(½H, d), 4.13(½H, d), 4.10(½H, d), 3.77(½H, d), 3.73(½H, d), 3.65(2H, m), 3.52(½H, d), 3.46(½H, d), 2.85(3/2H, s), 2.87(3/2H, s).

EXAMPLE 25

(6R,7R)7-[(RS)2-(2-Aminothiazol-4-yl)-2-(1,5-dihydroxy-4-pyridone-2-carboxamido)acetamido]-3-(1,2,3-thiadiazol-5-yl)thiomethyl-ceph-3-em-4-carboxylic acid (A): 5-Mercapto-1,2,3-thiadiazole NMR(D$_2$O) δ: 8.69(½H, s), 8.68(½H, s), 7.61(1H, s), 7.37(1H, s), 6.78(½H, s), 5.68(½H, d), 5.60(½H, s), 5.59(½H, s), 5.59(½H, d), 5.09(½H, d), 5.06(½H, d), 4.37(½H, d), 4.32(½H, d), 3.92(½H, d), 3.90(½H, d), 3.71(½H, d), 3.67(½H, d), 3.40(½H, d), 3.34(½H, d).

EXAMPLE 26

(6R,7R)7-[(RS)2-(2-Aminothiazol-4-yl)-2-(1,5-dihydroxy-4-pyridone-2-carboxamido)acetamido]-3-(benzothiazol-2-yl)thiomethyl-ceph-3-em-4-carboxylic acid (A): 2-Mercaptobenzothiazole NMR(D$_2$O) δ: 7.81(1H, d), 7.76(1H, d), 7.55(½H, s), 7.53(½H, s), 7.46(1H, m), 7.36(1H, m), 7.31(½H, s), 7.27(½H, s), 6.73(½H, s), 6.70(½H, S), 5.66(½H, d), 5.56(1H, s), 5.56(½H, d), 5.01(½H, d), 4.96(½H, d), 4.53(½H, d), 4.49(½H, d), 4.06(½H, d), 4.02(½H, d), 3.68(½H, d), 3.63(½H, d), 3.38(½H, d), 3.30(½H, d).

EXAMPLE 27

(6R,7R)7-[(RS)2-(2-Aminothiazol-4-yl)-2-(1,5-dihydroxy-4-pyridone-2-carboxamido)acetamido]-3-(2,5-dihydro-2-methyl-5-oxo-6-hydroxy-1,2,4-triazin-3-yl)thiomethyl-ceph-3-em-4-carboxylic acid (A): 3-Mercapto-2,5-dihydro-2-methyl-5-oxo-6-hydroxy-1,2,4-triazine NMR(D$_2$O) δ: 3.50(½×2H, ABq), 3.58(½×2H, ABq), 3.65, 3.66(each ½×3H, s), 4.21(½×2H, ABq), 4.24(½×2H, ABq), 5.04(1H, s), 5.10(½H, d), 5.14(½H, d), 5.63(½H, d), 5.72(½H, d), 6.75(½H, s), 6.80(½H, s), 7.35(½H, s), 7.36(½H, s), 7.58(1H, s).

EXAMPLE 28

(6R,7R)7-[(RS)2-(2-Aminothiazol-4-yl)-2-(1,5-dihydroxy-4-pyridone-2-carboxamido)acetamido]-3-(2-methyl-1,3,4-thiadiazol-5-yl)thiomethyl-ceph-3-em-4-carboxylic acid (A): 5-Mercapto-2-methyl-1,3,4-thiadiazole NMR(D$_2$O) δ: 7.71(1H, s), 7.45(1H, s), 6.80(½H, s), 6.73(½H, s), 5.67(½H, d), 5.59(½H, s), 5.58(½H, s), 5.58(½H, d), 5.08(½H, d), 5.05(½H, d), 4.50(½H, d), 4.48(½H, d), 3.93(½H, d), 3.89(½H, d), 3.78(½H, d), 3.75(½H, d), 3.40(½H, d), 3.34(½H, d), 2.72(3H, s).

EXAMPLE 29

(6R,7R)7-[(RS)2-(2-Aminothiazol-4-yl)-2-(1,5-dihydroxy-4-pyridone-2-carboxamido)acetamido]-3-(2-methylamino-1,3,4-thiadiazol-5-yl)-thiomethyl-ceph-3-em-4-carboxylic acid (A): 5-Mercapto-2-methylamino-1,3,4-thiadiazole NMR(D$_2$O) δ: 2.95, 2.96(each ½×3H, s), 3.44(½×2H, ABq), 3.52(½×2H, ABq), 4.30(½×2H, ABq), 4.33(½×2H, ABq), 5.04(½H, d), 5.10(½H, d), 5.60(½H, d), 5.61(1H, s), 5.67(½H, d), 6.76(½H, s), 6.80(½H, s), 7.42(½H, s), 7.43(½H, s), 7.66(1H, s).

EXAMPLE 30

(6R,7R)7-[(RS)2-(2-Aminothiazol-4-yl)-2-(1,5-dihydroxy-4-pyridone-2-carboxamido)acetamido]-3-(benzimidazol-2-yl)thiomethyl-ceph-3-em-4-carboxylic acid (A): 2-Mercaptobenzimidazole NMR(D$_2$O) δ: 7.65–7.1(6H, m), 6.83(½H, s), 6.79(½H, s), 5.73(½H, d), 5.69(½H, d), 5.65(½H, s), 5.64(½H, s), 5.19(½H, d), 5.11(½H, d), 4.51(½H, d), 4.47(½H, d), 3.98(½H, d), 3.95(½H, d), 3.81(½H, d), 3.76(½H, d), 3.55(½H, d), 3.50(½H, d).

EXAMPLE 31

(6R,7R)7-[(RS)2-(2-Aminothiazol-4-yl)-2-(1,5-dihydroxy-4-pyridone-2-carboxamido)acetamido]-3-(benzoxazol-2-yl)thiomethyl-ceph-3-em-4-carboxylic acid (A): 2-Mercaptobenzoxazole NMR(D$_2$O) δ: 7.60(3H, m), 7.37(3H, m), 6.77(½H, s), 6.73(½H, s), 5.65(½H, d), 5.57(½H, s), 5.55(½H, s), 5.56(½H, d), 5.06(½H, d) 5.02(½H, d) 4.71(½H, d), 4.68(½H, d), 4.03(½H, d), 3.99(½H, d), 3.81(½H, d), 3.78(½H, d), 3.45(½H, d), 3.38(½H, d).

EXAMPLE 32

(6R,7R)7-[(RS)2-(2-Aminothiazol-4-yl)-2-(1,5-dihydroxy-4-pyridone-2-carboxamido)acetamido]-3-(5-methyl-s-triazolo[1,5-a]pyrimidin-7-yl)thiomethyl-ceph-3-em-4-carboxylic acid (A): 7-Mercapto-5-methyl-s-triazolo[1,5-a]pyrimidine NMR(D$_2$O) δ: 2.61(3H, s), 3.43(½H, d), 3.48(½H, d), 3.71(½H, d), 3.75(½H, d), 4.19(½H+½H, m), 4.50(½H, d), 4.54(½H, d), 5.08(½H, d), 5.11(½H, d), 5.58(½H, d), 5.63(½H, d), 5.72(½H, d), 6.72(½H, s), 6.77(½H, s), 7.17(1H, s), 7.32(½H, s), 7.33(½H, s), 7.57(1/8 H, s), 7.59(½H, s), 8.45(½H, s), 8.46(½H, s).

EXAMPLE 33

(6R,7R)7-[(RS)2-(2-Aminothiazol-4-yl)-2-(1,5-dihydroxy-4-pyridone-2-carboxamido)acetamido]-3-(3-trifluoromethyl-4-methyl-4H-1,2,4-triazol-5-yl)thiomethyl-ceph-3-em-4-carboxylic acid (A): 5-Mercapto-4-methyl-3-trifluoromethyl-4H-1,2,4-triazole NMR(D$_2$O) δ: 3.37(½H, d), 3.44(½H, d), 3.68–3.86(2H, m), 3.84(3H, s), 4.28(½H, d), 4.33(½H, d), 5.07(½H, s), 5.10(½H, s), 5.59(½H, d), 5.60(½H, s), 5.61(½H, s), 5.68(½H, d), 6.75(½H, s), 6.80(½H, s), 7.40(1H, s), 7.63(1H, s).

EXAMPLE 34

(6R,7R)7-[(RS)2-(2-Aminothiazol-4-yl)-2-(1,5-dihydroxy-4-pyridone-2-carboxamido)acetamido]-3-(pyrimidin-2-yl)thiomethyl-ceph-3-em-4-carboxylic acid (A): 2-Mercaptopyrimidine NMR(D$_2$O) δ: 3.35(½H, d), 3.42(½H, d), 3.8(½H, m), 4.21(1H, m), 4.65(1H, m), 5.03(½H, d), 5.07(½H, d), 5.61(1H, s), 5.63(½H, d), 5.69(½H, d), 6.75(½H, s), 6.81(½H, s), 7.22(1H, t), 7.41(1H, s), 7.68(1H, s), 8.58(2H, m).

EXAMPLE 35

(6R,7R)7-[(RS)2-(2-Aminothiazol-4-yl)-2-(1,5-dihydroxy-4-pyridone-2-carboxamido)acetamido]-3-(4-carboxy-3-hydroxyisothiazol-5-yl)thiomethyl-ceph-3-em-4-carboxylic acid (A): 4-Carboxy-3-hydroxy-5-mercaptoisothiazole NMR(D$_2$O) δ: 3.42(½H, d), 3.48(½H, d), 3.63(½H, d), 3.68(½H, d), 4.29(2H, m), 5.12(½H, d), 5.17(½H, d), 5.63(½H, d), 5.64(1H, s), 5.74(½H, d), 6.78(½H, s), 6.82(½H, s), 7.44(1H, s), 7.68(1H, s).

EXAMPLE 36

(6R,7R)7-[(RS)2-(2-Aminothiazol-4-yl)-2-(1,5-dihydroxy-4-pyridone-2-carboxamido)acetamido]-3-(4-cyano-3-hydroxyisothiazol-5-yl)thiomethyl-ceph-3-em-4-carboxylic acid (A): 4-Cyano-3-hydroxy-5-mercaptoisothiazole NMR(D$_2$O) δ: 3.41(½H, d), 3.50(½H, d), 3.63(½H, d), 3.68(½H, d), 4.30(2H, m), 5.13(½H, d), 5.18(½H, d), 5.63(½H, d), 5.64(1H, s), 5.75(½H, d), 5.78(½H, d), 6.82(½H, s), 7.44(1H, s), 7.66(1H, s).

EXAMPLE 37

(6R,7R)7-[(RS)2-(2-Aminothiazol-4-yl)-2-(1,5-dihydroxy-4-pyridone-2-carboxamido)acetamido]-3-(2-carboxy-1-methylpyridinium-4-yl)thiomethyl-ceph-3-em-4-carboxylate (A): 2-Carboxy-1-methyl-4-thiopyridone NMR($D_2O$) δ: 3.36($\frac{1}{2}$H, d), 3.42($\frac{1}{2}$H, d), 3.65($\frac{1}{2}$H, d), 3.69($\frac{1}{2}$H, d), 4.15(1H, m), 4.16(3H, s), 4.33($\frac{1}{2}$H, d), 4.37($\frac{1}{2}$H, d), 5.07($\frac{1}{2}$H, d), 5.10($\frac{1}{2}$H, d), 5.57($\frac{1}{2}$H, s), 5.59($\frac{1}{2}$H, s), 5.60($\frac{1}{2}$H, d), 5.70($\frac{1}{2}$H, d), 6.72($\frac{1}{2}$H, s), 6.77($\frac{1}{2}$H, s), 7.38(1H, s), 7.62($\frac{1}{2}$H, s), 7.62($\frac{1}{2}$H, s), 7.69(1H, m), 7.79(1H, m), 8.32(1H, m).

EXAMPLE 38

(6R,7R)7-[(RS)2-(2-Aminothiazol-4-yl)-2-(1,5-dihydroxy-4-pyridone-2-carboxamido)acetamido]-3-(2,3-dihydro-1H-indolidinium-5-yl)thiomethyl-ceph-3-em-4-carboxylate (A): 2,3-Dihydro-5(1H)-indolidinethione NMR($D_2O$) δ: 2.46(2H, m), 3.41(1H, m), 3.50(2H, m), 3.67(1H, m), 4.20(1H, m), 4.44(1H, m), 4.64(2H, m), 5.03($\frac{1}{2}$H, d), 5.07($\frac{1}{2}$H, d), 5.56($\frac{1}{2}$H, d), 5.59(1H, s), 5.65($\frac{1}{2}$H, d), 6.73($\frac{1}{2}$H, s), 6.77($\frac{1}{2}$H, s), 7.38($\frac{1}{2}$H, s), 7.39($\frac{1}{2}$H, s), 7.61(1H, s), 7.63(1H, m), 7.68(1H, m), 8.13((1H, m).

EXAMPLE 39

(6R,7R)7-[(RS)2-(2-Aminothiazol-4-yl)-2-(1,5-dihydroxy-4-pyridone-2-carboxamido)acetamido]-3-(4-phenylthiazol-2-yl)thiomethyl-ceph-3-em-4-carboxylic acid (A): 2-Mercapto-4-phenylthiazole NMR($D_2O$) δ: 7.76((2H, d), 7.67(1H, s), 7.60($\frac{1}{2}$H, s), 7.57($\frac{1}{2}$H, s), 7.35-7.50(3H, m), 7.35($\frac{1}{2}$H, s), 7.33($\frac{1}{2}$H, s), 6.71($\frac{1}{2}$H, s), 6.68($\frac{1}{2}$H, s), 5.63($\frac{1}{2}$H, d), 5.54(($\frac{1}{2}$H, s), 5.53($\frac{1}{2}$H, d), 5.00($\frac{1}{2}$H, d), 4.95($\frac{1}{2}$H, d), 4.47($\frac{1}{2}$H, d), 4.43($\frac{1}{2}$H, d), 3.90($\frac{1}{2}$H, d), 3.88($\frac{1}{2}$H, d), 3.68($\frac{1}{2}$H, d), 3.62($\frac{1}{2}$H, d), 3.34($\frac{1}{2}$H, d), 3.26($\frac{1}{2}$H, d).

EXAMPLE 40

(6R,7R)7-[(RS)2-(2-Aminothiazol-4-yl)-2-(1,5-dihydroxy-4-pyridone-2-carboxamido)acetamido]-3-(1-methyl-1H-tetrazol-5-yl)thiomethyl-ceph-3-em-4-carboxylic acid In the same manner as the method A of the Example 1, with the exception that (6R,7R)7-[(RS)2-(2-aminothiazol-4-yl)-2-aminoacetamido]-3-(1-methyl-1H-tetrazol-5-yl)thiomethyl-ceph-3-em-4-carboxylic acid hydrochloride was used instead of (6R,7R)7-[(RS)2-(2-aminothiazol-4-yl)-2-aminoacetamido]-3-acetoxymethyl-ceph-3-em-4-carboxylic acid hydrochloride, the above-entitled compound was obtained. The spectral data of this compound were the same as those of the compound of the Example 21.

EXAMPLE 41

(6R,7R)7-[(RS)2-(2-Aminothiazol-4-yl)-2-(1,5-dihydroxy-4-pyridone-2-carboxamido)acetamido]-3-(1-methylpyridinium-4-yl)thiomethyl-ceph-3-em-4-carboxylate (a) 1.03 g of (RS)2-(2-tritylaminothiazol-4-yl)-2-(t-butoxycarbonylamino)acetic acid was dissolved in 10 ml of DMF, and 270 mg of 1-hydroxybenzotriazole and 412 mg of N,N'-dicyclohexylcarbodiimide were added thereto and reacted for 1 hour at room temperature. To this was added 10 ml of DMF-solution containing 740 mg of benzhydryl 7-amino-3-chloromethyl-ceph-3-em-4-carboxylate and reacted for 5 hours at room temperature. After the reaction, the insoluble part was filtrated out, and 120 ml of ethyl acetate was added to the remaining filtrate solution, which was thereafter washed with dilute sodium hydrogencarbonate aqueous solution, dilute hydrochloric acid aqueous solution and saturated salt aqueous solution in this order and then dried with magnesium sulfate and concentrated to drying under reduced pressure. The residue formed was purified with silicagel-column chromatography (benzene/ethyl acetate=8/1), to obtain 1.3 g of benzhydryl(6R,7R)7-[(RS)2-(2-aminothiazol-4-yl)-2-(t-butoxycarbonylamino)acetamido]-3-chloromethyl-ceph-3-em-4-carboxylate.

(b) 1.05 g of the product as above obtained was dissolved in 15 ml of tetrahydrofuran, and 180 mg of 1-methyl-4-thiopyridone was added thereto and reacted for 5 hours at room temperature. After the reaction, the reaction solution was concentrated, 20 ml of ethyl acetate was added to the resulting residue and the precipitate formed was taken out by filtration and then washed with ethyl acetate. After filtrated, 1 g of benzhydryl(6R,7R)7-[(RS)2-(2-tritylaminothiazol-4-yl)-2-(t-butoxycarbonylamino)acetamido]-3-(1-methylpyridinium-4-yl)thiomethyl-ceph-3-em-4-carboxylate was obtained.

(c) 980 mg of the product as above obtained was suspended in 3.3 ml of anisole, and 15 ml of trifluoroacetic acid was added thereto, while cooled with ice, and reacted for 30 minutes at room temperature. After the reaction, the reaction solution was added dropwise to 100 ml of diisopropylether, and the precipitate formed therein was taken out by filtration and dried to obtain 720 mg of (6R,7R)7-[(RS)2-(2-aminothiazol-4-yl)-2-aminoacetamido]-3-(1-methylpyridinium-4-yl)thiomethyl-ceph-3-em-4-carboxylate trifluoroacetate.

NMR($D_2O$) δ: 3.49($\frac{1}{2}$H, d), 3.56($\frac{1}{2}$H, d), 3.75($\frac{1}{2}$H, d), 3.77($\frac{1}{2}$H, d), 4.22(3H, s), 4.3-4.5(2H, m), 5.16($\frac{1}{2}$H, d), 5.18($\frac{1}{2}$H, d), 5.32($\frac{1}{2}$H, s), 5.33($\frac{1}{2}$H, s), 5.65($\frac{1}{2}$H, d), 5.77($\frac{1}{2}$H, d), 7.12(1H, s), 7.81(2H, m), 8.43(2H, d).

(d) 380 mg of 5-p-methoxybenzyloxy-1-hydroxy-4-pyridone-2-carboxylic acid was suspended in 6 ml of tetrahydrofuran, and 0.24 ml of triethylamine was added thereto and dissolved. 220 mg of phosphorus pentachloride was added thereto at −10° to −15° C. and reacted for 1 hour at the same temperature, to obtain an acid chloride solution.

670 mg of (6R,7R)7-[(RS)2-(2-aminothiazol-4-yl)-2-aminoacetamido]-3-(1-methylpyridinium-4-yl)thiomethyl-ceph-3-em-4-carboxylate trifluoroacetate, as obtained in the above (c), was dissolved in 3 ml of tetrahydrofuran and 9 ml of water, and then the previously prepared acid chloride-solution was added thereto, while the reaction system was cooled with ice and was regulated to have a pH of 8–8.5 with triethylamine. After the reaction, the reaction solution was concentrated under reduced pressure to remove tetrahydrofuran therefrom, and 6N-HCl was added thereto, while cooled with ice, to adjust the pH thereof to 2, and the precipitate formed was taken out by filtration. After washed with water and dried, 550 mg of a crude powder of (6R,7R)7-[(RS)2-(2-aminothiazol-4-yl)-2-(5-p-methoxybenzyloxy-1-hydroxy-4-pyridone-2-carboxamido)acetamido]acetamido]-3-(1-methylpyridinium-4-myl)thiomethyl-ceph-3-em-4-carboxylate was obtained.

(e) The product obtained in (d) was suspended in 1.5 ml of anisole and 6 ml of trifluoroacetic acid was added thereto, while cooled with ice, and reacted for 30 minutes at room temperature.

After the reaction, the reaction solution was added to 60 ml of diisopropylether, and the precipitate formed was taken out by filtration and dried. This was suspended in a small amount of water, and saturated sodium hydrogencarbonate aqueous solution was added thereto and dissolved (pH 7-7.2), and the resulting solution was purified with HP-20 column-chromatography (eluent: 5% acetone aqueous solution), to obtain 240 mg of the above entitled compound. The spectral data of this compound were the same as those of the same compound of the Example 2.

EXAMPLE 42

(6R,7R)7-[(RS)2-(2-Aminothiazol-4-yl)-2-(1,5-dihydroxy-4-pyridone-2-carboxamido)acetamido]-3-(1,2,3-thiadiazol-5-yl)thiomethyl-ceph-3-em-4-carboxylic acid (a) 520 mg of 5-benzyloxy-1-hydroxy-4-pyridone-2-carboxylic acid was suspended in 7 ml of tetrahydrofuran, and 0.36 ml of triethylamine was added thereto and dissolved. 420 mg of phosphorus pentachloride was added thereto at −10° C. and reacted for 1 hour, to obtain an acid chloride solution.

On the other hand, 600 mg of (RS)2-(2-tritylaminothiazol-4-yl)glycine was dissolved in 20 ml of 50% -tetrahydrofuran aqueous solution. To this was added the previously prepared acid chloride solution little by little, while the pH value of the reaction solution was kept to be 8–8.5 with triethylamine and cooled with ice.

After the reaction, the reaction solution was concentrated under reduced pressure to remove tetrahydrofuran therefrom, and 6N-HCl was added to the residue to regulate the pH of the solution to 2, which was then extracted with chlorform (100 ml×2). After washed with water, the liquid was dried with magnesium sulfate and concentrated to drying to obtain 1.0 g of (RS)2-(2-tritylaminothiazol-4-yl)-2-(5-benzyloxy-1-hydroxy-4-pyridone-2-carboxamido)acetic acid.

(b) 660 mg of the product obtained above was dissolved in 5 ml of tetrahydrofuran, and 0.15 ml of triehtylamine and 210 mg of phosphorus pentachloride were added thereto at 10° C. and reacted for 1 hour at the same temperature.

On the other hand, 250 mg of 7-amino-3-(1,2,3-thiadiazol-5-yl)thiomethyl-ceph-3-em-4-carboxylic acid was suspended in 50%-tetrahydrofuran aqueous solution, and triethylamine was added thereto, while cooled with ice, and dissolved at pH 8. To this was added the previously prepared reaction solution little by little, while the pH value of the reaction solution was kept to be 8–8.5 with triethylamine as added.

After the reaction, the reaction solution was concentrated under reduced pressure to remove tetrahydrofuran therefrom, and then, water was added thereto and the resulting solution was regulated to have a pH of 2 with 6N-HCl, which was thereafter extracted with ethyl acetate. After washed with water, the liquid was dried with magnesium sulfate and concentrated to drying, to obtain 790 mg of (6R,7R)7-[(RS)2-(2-tritylaminothiazol-4-yl)-2-(5-benzyloxy-1-hydroxy-4-pyridone-2-carboxamido)acetamido]-3-(1,2,3-thiadiazol-5-yl)thiomethyl-ceph-3-em-4-carboxylic acid.

(c) This was dissolved in 7 ml of formic acid, and 0.3 ml of concentrated hydrochloric acid was added thereto and reacted for 1 hour at room temperature. After the reaction, the precipitate formed was filtrated out, and the remaining filtrate solution was concentrated to a small amount and then washed with ether.

The residue obtained was suspended in a small amount of water and then dissolved, as regulated to have a pH of 7 with saturated sodium hydrogencarbonate aqueous solution. The resulting solution was purified with HP-20 column-chromatography (eluent: 10–20% acetone/water) to obtain 320 mg of sodium(6R,7R)7-[(RS)2-(2-aminothiazol-4-yl)-2-(5-benzyloxy-1-hydroxy-4-pyridone-2-carboxamido)acetamido]-3-(1,2,3-thiazol-5-yl)thiomethyl-ceph-3-em-4-carboxylate.

Next, this was subjected to catalytic hydrogenation in the same manner as the step (b) in the Example 1, to obtain the above-entitled compound. The spectral data of this compound were the same as those of the same compound of the Example 25.

EXAMPLE 43

Preparations for injection

The compound of the Example 2 was filled in vials under sterile condition, each in an amount of 1000 mg (titer).

EXAMPLE 44

| Capsules | |
| --- | --- |
| Compound of Example 2 | 250 parts (titer) |
| Lactose | 60 parts |
| Magnesium stearate | 5 parts |

These were blended uniformly, and the resulting mixture was encapsulated in an amount of 250 mg (titer)/one capsule.

EXAMPLE 45

| Soft capsules for per-rectal application | |
| --- | --- |
| Olive oil | 160 parts |
| Polyoxyethylenelaurylether | 10 parts |
| Sodium hexametaphosphate | 5 parts |

These were blended uniformly to obtain a base component. 25 parts (titer) of the compound of the Example 2 were added to the base component and further uniformly blended and then encapsulated in soft capsules each in an amount of 250 mg (titer)/one capsule, to obtain soft capsules for per-rectal application.

What is claimed is:

1. Cephalosporin compounds represented by the following formula (I) and pharmaceutically acceptable salts thereof:

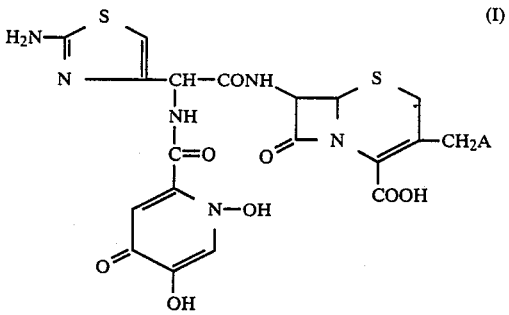 (I)

wherein A represents an unsubstituted or substituted pyridylthio group of a formula (I-1):

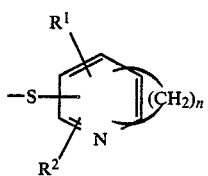 (I-1)

(where n is 0 or an integer of 3–5; $R^1$ and $R^2$ may be the same or different and each represent a hydrogen atom, a halogen atom, a carboxyl group or an optionally halogen-substituted lower alkyl group having 1–5 carbon atoms); or an unsubstituted or substituted pyridiniumthio group of a formula (I-2):

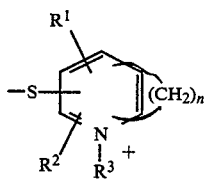 (I-2)

[where n, $R^1$ and $R^2$ have the same meanings as above; $R^3$ represents a linear or branched alkyl group having 1–5 carbon atoms, a halogen-substituted alkyl group, a cyclopropyl group, a cyclopropylmethyl group, an alkenyl group, an oxygen atom or a group of —($CH_2$)$_m$—B; (m is an integer of 0–3; and B represents a hydroxyl group, an alkoxy group, an amino group, an alkyl-substituted amino group, a carboxyl group, a carbamoyl group, a sulfonic acid group, a sulfonic acid amide group, a hydroxamic acid group, a cyano group, a thiol group, an alkylthio group, a methanesulfonylaminocarbonyl group or an acetamidosulfonyl group)]; or an unsubstituted or substituted pyridinium group of a formula (I-3):

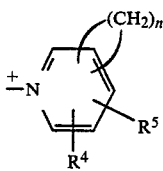 (I-3)

(where n has the same meaning as above; $R^4$ and $R^5$ may be the same or different and each represent a hydrogen atom, a linear or branched alkyl group having 1–5 carbon atoms, a carboxyl group, a carbamoyl group, a sulfonic acid group, a sulfonic acid amide group, a linear or branched alkylthio group having 1–5 carbon atoms, a halogen-substituted alkylthio group, a cycloalkanothio group, a cycloalkanomethylthio group, a carboxyalkylthio group, a carbamoylalkylthio group, an alkoxyalkylthio group or an alkylsubstituted aminoalkylthio group); or a 5- or 6-membered heterocyclicthio or bicycloheterocyclicthio group of a formula (I-4):

—S—Het (I-4)

(where Het represents an optionally substituted thiazole, isothiazole, 1,2,3-thiadiazole, 1,3,4-thiadiazole, 1,3,4-triazole, 1,2,3,4-tetrazole, pyrimidine, 1,2,4-triazine, benzothiazole, benzimidazole, benzoxazole, 1,3,4-triazaindolidine or 2,3-dihydro-1H-indolidinium group).

2. (6R,7R)7-[(RS)2-(2-aminothiazol-4-yl)-2-(1,5-dihydroxy-4-pyridone-2-carboxamido)acetamido]-3-[1-(2-hydroxy)ethylpyridinium-4-yl]thiomethyl-ceph-3-em-4-carboxylate according to claim 1.

3. (6R,7R)7-[(RS)2-(2-aminothiazol-4-yl)-2-(1,5-dihydroxy-4-pyridone-2-carboxamido)acetamido]-3-(1-cyclopropyl-pyridinium-4-yl)thiomethyl-ceph-3-em-4-carboxylate according to claim 1.

4. (6R,7R)7-[(RS)2-(2-aminothiazol-4-yl)-2-(1,5-dihydroxy-4-pyridone-2-carboxamido)acetamido]-3-(1-methylpyridinium-4-yl)thiomethyl-ceph-3-em-4-carboxylate according to claim 1.

5. (6R,7R)7-[(RS)2-(2-aminothiazol-4-yl)-2-(1,5-dihydroxy-4-pyridone-2-carboxamido)acetamido]-3-(1-carboxymethyl-pyridinium-4-yl)thiomethyl-ceph-3-em-4-carboxylate according to claim 1.

6. (6R,7R)7-[(RS)2-(2-aminothiazol-4-yl)-2-(1,5-dihydroxy-4-pyridone-2-carboxamido)acetamido]-3-(1-carbamoylmethyl-pyridinium-4-yl)thiomethyl-ceph-3-em-4-carboxylate according to claim 1.

7. (6R,7R)7-[(RS)2-(2-aminothiazol-4-yl)-2-(1,5-dihydroxy-4-pyridone-2-carboxamido)acetamido]-3-(2,3-cyclopenteno-1-carboxymethyl-pyridinium-4-yl)thiomethyl-ceph-3-em-4-carboxylate according to claim 1.

8. (6R,7R)7-[(RS)2-(2-aminothaizol-4-yl)-2-(1,5-dihydroxy-4-pyridone-2-carboxamido)acetamido]-3-(1-methylpyridinium-3-yl)thiomethyl-ceph-3-em-4-carboxylate according to claim 1.

9. (6R,7R)7-[(RS)2-(2-aminothiaozl-4-yl)-2-(1,5-dihydroxy-4-pyridone-2-carboxamido)acetamido]-3-[1-(2-sulfamoyl)ethylpyridinium-4-yl]thiomethyl-ceph-3-em-4-carboxylate according to claim 1.

10. (6R,7R)7-[(RS)2-(2aminothiazol-4-yl)-2-(1,5-dihydroxy-4-pyridone-2-carboxamido)acetamido]-3-(1,2,3-thiadiazol-5-yl)thiomethyl-ceph-3-em-4-carboxylate according to claim 1.

11. (6R,7R)7-[(RS)2-(2-aminothiazol-4-yl)-2-(1,5-dihydroxy-4-pyridone-2-carboxamido)acetamido]-3-(2,3-cyclopenteno-pyridinium)methyl-ceph-3-em-4-carboxylate according to claim 1.

12. (6R,7R)7-[(RS)2-(2-aminothiazol-4-yl)-2-(1,5-dihydroxy-4-pyridone-2-carboxamido)acetamido]-3-(4-methylthiopyridinium)methyl-ceph-3-em-4-carboxylate according to claim 1.

13. (6R,7R)7-[(RS)2-(2-aminothiazol-4-yl)-2-(1,5-dihydroxy-4-pyridone-2-carboxamido)acetamido]-3-(1-methyltetrazol-5-yl)thiomethyl-ceph-3-em-4-carboxylate according to claim 1.

14. (6R,7R)7-[(RS)2-(2-aminothiazol-4-yl)-2-(1,5-dihydroxy-4-pyridone-2-carboxamido)acetamido]-3-

(benzothiazol-2-yl)thiomethyl-ceph-3-em-4-carboxylate according to claim 1.

15. (6R,7R)7-[(RS)2-(2-aminothiazol-4-yl)-2-(1,5-dihydroxy-4-pyridone-2-carboxamido)acetamido]-3-[1-(2-fluoroethyl)pyridinium-4-yl]thiomethyl-ceph-3-em-4-carboxylate according to claim 1.

16. (6R,7R)7-[(RS)2-(2-aminothiazol-4-yl)-2-(1,5-dihydroxy-4-pyridone-2-carboxamido)acetamido]-3-(pyridin-4-yl)thiomethyl-ceph-3-em-4-carboxylate according to claim 1.

17. An antibacterial pharmaceutical composition containing an effective amount of a compound of claim 1 and a pharmaceutically acceptable carrier.

* * * * *